US011338028B2

(12) United States Patent
Yan et al.

(10) Patent No.: US 11,338,028 B2
(45) Date of Patent: May 24, 2022

(54) CANCER VACCINES TARGETING LEMD1 AND USES THEREOF

(71) Applicant: Inovio Pharmaceuticals, Inc., Plymouth Meeting, PA (US)

(72) Inventors: Jian Yan, Wallingford, PA (US); Anna Slager, Landsdale, PA (US); Bradley Garman, Glenside, PA (US); Neil Cooch, Oreland, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 384 days.

(21) Appl. No.: 16/219,446

(22) Filed: Dec. 13, 2018

(65) Prior Publication Data
US 2019/0175712 A1    Jun. 13, 2019

Related U.S. Application Data

(60) Provisional application No. 62/598,612, filed on Dec. 14, 2017, provisional application No. 62/598,329, filed on Dec. 13, 2017.

(51) Int. Cl.
*C07K 14/47* (2006.01)
*A61P 35/00* (2006.01)
*A61K 39/00* (2006.01)

(52) U.S. Cl.
CPC ...... *A61K 39/001184* (2018.08); *C07K 14/47* (2013.01); *A61K 2039/53* (2013.01); *A61K 2039/54* (2013.01); *A61K 2039/572* (2013.01)

(58) Field of Classification Search
CPC ...... A61K 39/001184; A61K 2039/572; A61K 2039/54; A61K 2039/53; C07K 14/47; C07K 14/4748; A61P 35/00
USPC ........................................................ 536/23.1
See application file for complete search history.

(56) References Cited

U.S. PATENT DOCUMENTS

| 9,675,668 B2 | 6/2017 | Bangel et al. |
| 2004/0229277 A1* | 11/2004 | Frantz ............ C07K 16/18 435/6.16 |
| 2006/0281081 A1 | 12/2006 | Nakamura et al. |

FOREIGN PATENT DOCUMENTS

| RU | 2469044 C2 | 12/2012 |
| WO | 2003/024392 A2 | 3/2003 |
| WO | 2004/021010 A2 | 3/2004 |
| WO | 2007/060671 A2 | 5/2007 |

OTHER PUBLICATIONS

International Search Report and Written Opinion issued in PCT/US18/65534, dated Apr. 29, 2019.
Andrew A. Pakula; "Genetic Analysis of Protein Stability and Function"; Annu. Rev. Genet.; vol. 23; 1989; p. 289-310.
UNIPROTKB-B4DYE5 (B4DYE5_HUMAN) Sep. 23, 2008; 6 pages.
UNIPROTKB-Q68G75 (LEMD1_HUMAN) May 1, 2007; 13 pages.
GenBank Accession No. NM_001199050.2; *Homo sapiens* LEM domain containing 1 (LEMD1), transcript variant 1, mRNA; Feb. 16, 2021; 3 pages.
GenBank Accession No. NP_001185979.1; LEM domain-containing protein 1 isoform 1 [*Homo sapiens*]; Feb. 16, 2021; 3 pages.
Yuki et al.; "Isolation of LEM domain-containing 1, a novel testis-specific gene expressed in colorectal cancers"; Oncology Reports; vol. 12; 2004; p. 275-280.

* cited by examiner

*Primary Examiner* — Yan Xiao
(74) *Attorney, Agent, or Firm* — BakerHostetler

(57) ABSTRACT

Disclosed herein are nucleic acid molecules comprising one or more nucleic acid sequences that encode a mutated consensus LEMD1 antigen. Vectors, compositions, and vaccines comprising one or more nucleic acid sequences that encode a mutated consensus LEMD1 antigen are disclosed. Methods of treating a subject with a LEMD1-expressing tumor and methods of preventing a LEMD1-expressing tumor are disclosed. Mutated consensus LEMD1 antigen is disclosed.

20 Claims, 15 Drawing Sheets

Specification includes a Sequence Listing.

* denotes mutation for inhibition of BAF binding

Syn. Con. LEMD1F    MDVKCLSDCKLQNQLEKLGFSPGF LRGLQEHQAPESHMGLSPKRETTARKTRLIRAGEKKVSQWA
Native LEMD1F (hu)  MDVKCLSDCKLQNQLEKLGFSPGP  LRGLQEHQAPESHMGLSPKRETTARKTRL SRAGEKKVSQWA LEM domain IgELS Conserved 26aa
of LEM domain

* Denotes mutation for BAF binding

FIG. 5 pGX0001

Synthetic Consensus
LEMD1F

BamHI          XhoI pGX1432 hCMV Promoter

BamHI (731)

Synthetic Consensus
LEMD1F (742-999)

XhoI (1001)

bGH PolyA

KanR

FIG. 6

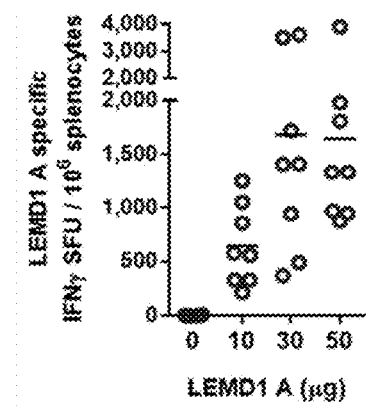
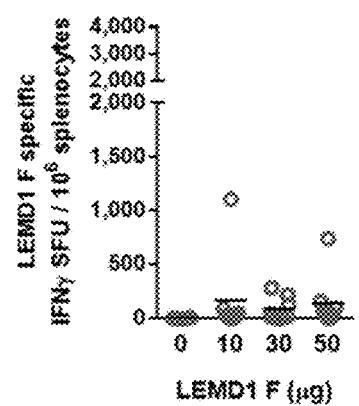
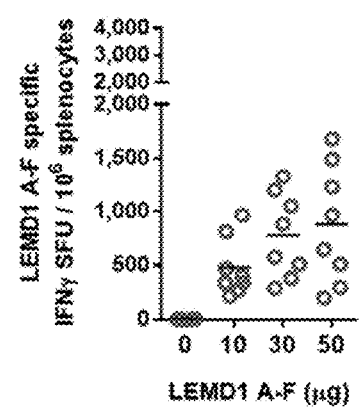
FIG. 11A　　　　　　　　FIG. 11B　　　　　　　　FIG. 11C
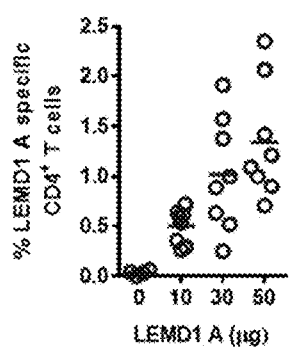
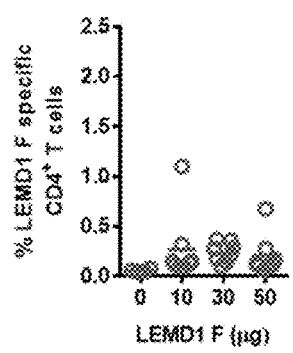
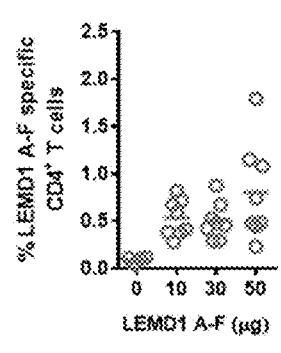
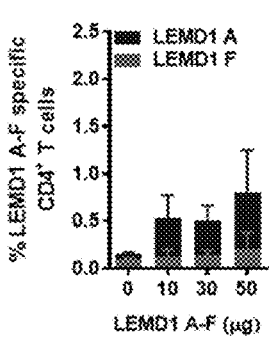
FIG. 12A　　　　FIG. 12B　　　　FIG. 12C　　　　FIG. 12D

CANCER VACCINES TARGETING LEMD1 AND USES THEREOF

CROSS-REFERENCE TO RELATED APPLICATIONS

This application claims priority to and the benefit of U.S. Provisional Patent Application No. 62/598,329, filed Dec. 13, 2017 and U.S. Provisional Patent Application No. 62/598,612 filed Dec. 14, 2017, the disclosures of which are incorporated herein by reference in their entirety.

SEQUENCE LISTING

This application contains a Sequence Listing which has been submitted electronically in ASCII format and is hereby incorporated by reference in its entirety. Said ASCII copy, created Nov. 23, 2021, is named 104409.000455_sequence-_listing.txt and is 30,462 bytes in size.

TECHNICAL FIELD

The present invention relates to LEMD1 antigens and nucleic acid molecules that encode the same. The present invention also relates to vaccines including such LEMD1 immunogens and/or nucleic acid molecules. The present invention further relates to methods of using the vaccines for inducing immune responses and preventing and/or treating subjects having cancer cells or tumors that express LEMD1.

BACKGROUND

Cancer remains a major cause of death in the U.S. and worldwide. The cancer vaccine market is growing rapidly. Effective tumor vaccines may be useful to prevent tumor growth and/or may be useful as being a more effective, less toxic alternative to standard treatments for patients with advanced cancers. An antigen associated with cancer and, therefore, a target for anti-tumor vaccines is LEMD1.

LEMD1 is a 20 kD protein that is localized to the inner nuclear membrane (INM). There, it associates with the nuclear lamina, which is involved in nuclear mechanical functions and heterochromatic organization. LEMD1 is characterized by its LAP2-Emerin-MAN1 (LEM) domain, initially described as a conserved globular module of approximately 40 amino acids that confers binding to Barrier-to-Autointegration Factor (BAF), a DNA bridging protein.

BAF-DNA nucleoprotein complexes play an important role in nuclear reassembly in association with lamins, and enhance de-condensation of chromatin at the end of mitosis. Increased expression of LEMD1 may be involved in the mitosis of rapidly-growing cancer cells. Yuki, D. et al., Isolation of LEM Domain-Containing 1, a Novel Testis-specific Gene Expressed in Colorectal Cancers. *Oncology reports* 12, 275-280 (2004). Six LEMD1 isoforms have been identified as LEMD1A through LEMD1F.

Vaccines for the treatment and prevention of cancer are of interest. However, existing vaccines targeting tumor cell antigens are limited by poor antigen expression in vivo. Accordingly, a need remains in the art for safe and effective vaccines and methods of their use for preventing and/or treating of cancer and reducing mortality in subjects suffering from cancer.

SUMMARY OF THE INVENTION

Disclosed herein are nucleic acid molecules comprising one or more nucleic acid sequences selected from the group consisting of (a) a nucleic acid sequence that encodes amino acid residues 19 to 198 of SEQ ID NO: 2; (b) a nucleic acid sequence that encodes amino acid residues 19 to 84 of SEQ ID NO: 4; (c) a nucleic acid sequence that encodes amino acid residues 19 to 198 and 206 to 271 of SEQ ID NO: 6; (d) a nucleic acid sequence that encodes a fragment comprising at least 90% of an entire length of a protein comprising amino acid residues 19 to 198 of SEQ ID NO: 2; (e) a nucleic acid sequence that encodes a fragment comprising at least 90% of an entire length of a protein comprising amino acid residues 19 to 84 of SEQ ID NO: 4; (i) a nucleic acid sequence that encodes a fragment comprising at least 90% of an entire length of a protein comprising amino acid residues 19 to 198 and 206 to 271 of SEQ ID NO: 6; (g) a nucleic acid sequence that encodes a protein that is greater than 95.6% identical to amino acid residues 19 to 198 of SEQ ID NO: 2; (h) a nucleic acid sequence that encodes a protein that is greater than 95.5% identical to amino acid residues 19 to 84 of SEQ ID NO: 4; (i) a nucleic acid sequence that encodes a protein that is at least 95% identical to amino acid residues 19 to 198 and 206 to 271 of SEQ ID NO: 6; (j) a nucleic acid sequence that encodes a fragment comprising at least 90% of an entire length of a protein that is greater than 95.6% identical to amino acid residues 19 to 198 of SEQ ID NO: 2; (k) a nucleic acid sequence that encodes a fragment comprising at least 90% of an entire length of a protein that is greater than 95.5% identical to amino acid residues 19 to 84 of SEQ ID NO: 4; and (1) a nucleic acid sequence that encodes a fragment comprising at least 90% of an entire length of a protein that is at least 95% identical to amino acid residues 19 to 198 and 206 to 271 of SEQ ID NO: 6.

Nucleic acid molecules are provided that comprise one or more nucleic acid sequences selected from the group consisting of (a) nucleotides 55 to 600 of SEQ ID NO: 1; (b) nucleotides 55 to 258 of SEQ ID NO: 3; (c) nucleotides 55 to 594 and 616 to 819 of SEQ ID NO: 5; (d) a fragment comprising at least 90% of an entire length a nucleic acid molecule comprising nucleotides 55 to 600 of SEQ ID NO: 1; (e) a fragment comprising at least 90% of an entire length a nucleic acid molecule comprising nucleotides 55 to 258 of SEQ ID NO: 3; (f) a fragment comprising at least 90% of an entire length a nucleic acid molecule comprising nucleotides 55 to 594 and 616 to 819 of SEQ ID NO: 5; (g) a fragment that is at least 95% identical to nucleotides 55 to 600 of SEQ ID NO: 1; (h) a fragment that is at least 95% identical to nucleotides 55 to 258 of SEQ ID NO: 3; (i) a fragment that is at least 95% identical to nucleotides 55 to 594 and 616 to 819 of SEQ ID NO: 5; (j) a fragment comprising at least 90% of an entire length of a nucleic acid sequence that is at least 95% identical to nucleotides 55 to 600 of SEQ ID NO: 1; (k) a fragment comprising at least 90% of an entire length of a nucleic acid sequence that is at least 95% identical to nucleotides 55 to 258 of SEQ ID NO: 3; and (1) a fragment comprising at least 90% of an entire length of a nucleic acid sequence that is at least 95% identical to nucleotides 55 to 594 and 616 to 819 of SEQ ID NO: 1. In some embodiments, the nucleic acid molecule comprises the nucleic acid sequence set forth in SEQ ID NO: 1, 3, or 5.

Also provided are nucleic acid molecules as described herein, wherein the nucleic acid molecule is incorporated into a plasmid or vector. In some embodiments, the nucleic acid molecule may be operably linked to a regulatory element selected from a promoter and a poly-adenylation signal. In some embodiments, the promoter is a human cytomegalovirus immediate-early promoter (hCMV promoter). In still other embodiments, the poly-adenylation signal may be a bovine growth hormone poly-adenylation signal (bGH polyA). In still further embodiments, the nucleic acid molecule may be incorporated into a viral vector.

Compositions are also disclosed that comprise one or more nucleic acid molecules as set forth herein. In some aspects, these compositions further comprise a pharmaceutically acceptable carrier.

Also provided herein are proteins and peptides comprising the amino acid sequence selected from the group consisting of (a) amino acid residues 19 to 198 of SEQ ID NO: 2; (b) amino acid residues 19 to 84 of SEQ ID NO: 4; (c) amino acid residues 19 to 198 and 206 to 271 of SEQ ID NO: 6; (d) a fragment comprising at least 90% of an entire length of amino acid residues 19 to 198 of SEQ ID NO: 2; (e) a fragment comprising at least 90% of an entire length of amino acid residues 19 to 84 of SEQ ID NO: 4; (f) a fragment comprising at least 90% of an entire length of amino acid residues 19 to 198 and 206 to 271 SEQ ID NO: 6; (g) an amino acid sequence that is greater than 95.6% identical to amino acid residues 19 to 198 of SEQ ID NO: 2; (h) an amino acid sequence that is greater than 95.5% identical to amino acid residues 19 to 84 of SEQ ID NO: 4; (i) an amino acid sequence that is at least 95% identical to amino acid residues 19 to 198 and 206 to 271 of SEQ ID NO: 6; (j) a fragment comprising at least 90% of an entire length of an amino acid sequence that is greater than 95.6% identical to amino acid sequences 19 to 198 of SEQ ID NO: 2; (k) a fragment comprising at least 90% of an entire length of an amino acid sequence that is greater than 95.5% identical to amino acid sequences 19 to 84 of SEQ ID NO: 4; and (1) a fragment comprising at least 90% of an entire length of an amino acid sequence that is at least 95% identical to amino acid sequences 19 to 198 and 206 and 271 of SEQ ID NO: 6.

Vaccines are also provided herein that comprise an antigen, wherein the antigen comprises the amino acid sequence selected from the group consisting of (a) amino acid residues 19 to 198 of SEQ ID NO: 2; (b) amino acid residues 19 to 84 of SEQ ID NO: 4; (c) amino acid residues 19 to 198 and 206 to 271 of SEQ ID NO: 6; (d) a fragment comprising at least 90% of an entire length of amino acid residues 19 to 198 of SEQ ID NO: 2; (e) a fragment comprising at least 90% of an entire length of amino acid residues 19 to 84 of SEQ ID NO: 4; (f) a fragment comprising at least 90% of an entire length of amino acid residues 19 to 198 and 206 to 271 SEQ ID NO: 6; (g) an amino acid sequence that is greater than 95.6% identical to amino acid residues 19 to 198 of SEQ ID NO: 2; (h) an amino acid sequence that is greater than 95.5% identical to amino acid residues 19 to 84 of SEQ ID NO: 4; (i) an amino acid sequence that is at least 95% identical to amino acid residues 19 to 198 and 206 to 271 of SEQ ID NO: 6; (j) a fragment comprising at least 90% of an entire length of an amino acid sequence that is greater than 95.6% identical to amino acid sequences 19 to 198 of SEQ ID NO: 2; (k) a fragment comprising at least 90% of an entire length of an amino acid sequence that is greater than 95.5% identical to amino acid sequences 19 to 84 of SEQ ID NO: 4; and (1) a fragment comprising at least 90% of an entire length of an amino acid sequence that is at least 95% identical to amino acid sequences 19 to 198 and 206 and 271 of SEQ ID NO: 6.

In some embodiments, the antigen of the vaccine is encoded by nucleic acid molecule comprising one or more nucleic acid sequences selected from the group consisting of (a) nucleotides 55 to 600 of SEQ ID NO: 1; (b) nucleotides 55 to 258 of SEQ ID NO: 3; (c) nucleotides 55 to 594 and 616 to 819 of SEQ ID NO: 5; (d) a fragment comprising at least 90% of an entire length a nucleic acid molecule comprising nucleotides 55 to 600 of SEQ ID NO: 1; (e) a fragment comprising at least 90% of an entire length a nucleic acid molecule comprising nucleotides 55 to 258 of SEQ ID NO: 3; (f) a fragment comprising at least 90% of an entire length a nucleic acid molecule comprising nucleotides 55 to 594 and 616 to 819 of SEQ ID NO: 5; (g) a fragment that is at least 95% identical to nucleotides 55 to 600 of SEQ ID NO: 1; (h) a fragment that is at least 95% identical to nucleotides 55 to 258 of SEQ ID NO: 3; (i) a fragment that is at least 95% identical to nucleotides 55 to 594 and 616 to 819 of SEQ ID NO: 5; (j) a fragment comprising at least 90% of an entire length of a nucleic acid sequence that is at least 95% identical to nucleotides 55 to 600 of SEQ ID NO: 1; (k) a fragment comprising at least 90% of an entire length of a nucleic acid sequence that is at least 95% identical to nucleotides 55 to 258 of SEQ ID NO: 3; and (1) a fragment comprising at least 90% of an entire length of a nucleic acid sequence that is at least 95% identical to nucleotides 55 to 594 and 616 to 819 of SEQ ID NO: 1.

Additional vaccines are provided comprising a nucleic acid molecule wherein the nucleic acid molecule comprises a nucleic acid sequence having at least about 95% identity over an entire length of the nucleic acid sequence set forth in SEQ ID NO: 1, 3, or 5.

Also disclosed herein are vaccines comprising a nucleic acid molecule wherein the nucleic acid molecule encodes a peptide comprising an amino acid sequence having at least about 95% identity over an entire length of the amino acid sequence set forth in SEQ ID NO: 2, 4, or 6. In some embodiments, the nucleic acid molecule may be an expression vector. In some embodiments, the vaccine further comprises a pharmaceutically acceptable excipient or an adjuvant.

Vaccines are also disclosed that comprise a peptide, wherein the peptide comprises an amino acid sequence having at least about 90% identity over an entire length of the amino acid sequence set forth in SEQ ID NO: 2, 4, or 6.

Also provided herein are methods of treating a subject with an LEMD1-expressing cancerous cell comprising administering a therapeutically effective amount of a vaccine described herein.

Methods of vaccinating a subject against an LEMD1-expressing cancerous cell comprising administering an amount of a vaccine as described herein effective to induce a humoral immune response.

BRIEF DESCRIPTION OF THE DRAWINGS

FIG. 5 is a schematic representation of synthetic consensus LEMD1F.

FIG. 6 illustrates the cloning strategy employed to generate pGX1432.

FIG. 11A, FIG. 11B, and FIG. 11C graphically illustrate the immunogenicity of synthetic consensus LEMD1A, synthetic consensus LEMD1F, and synthetic consensus LEMD1AF, respectively.

FIG. 12A, FIG. 12B, and FIG. 12C graphically illustrate the relative frequency of CD4+ T-cells induced by synthetic consensus LEMD1A, synthetic consensus LEMD1F, and synthetic consensus LEMD1AF, respectively. FIG. 12D compares the relative frequencies of CD4+ T-cells induced by synthetic consensus LEMD1A and synthetic consensus LEMD1F.

DETAILED DESCRIPTION OF THE INVENTION

Figures 1A, 1B:
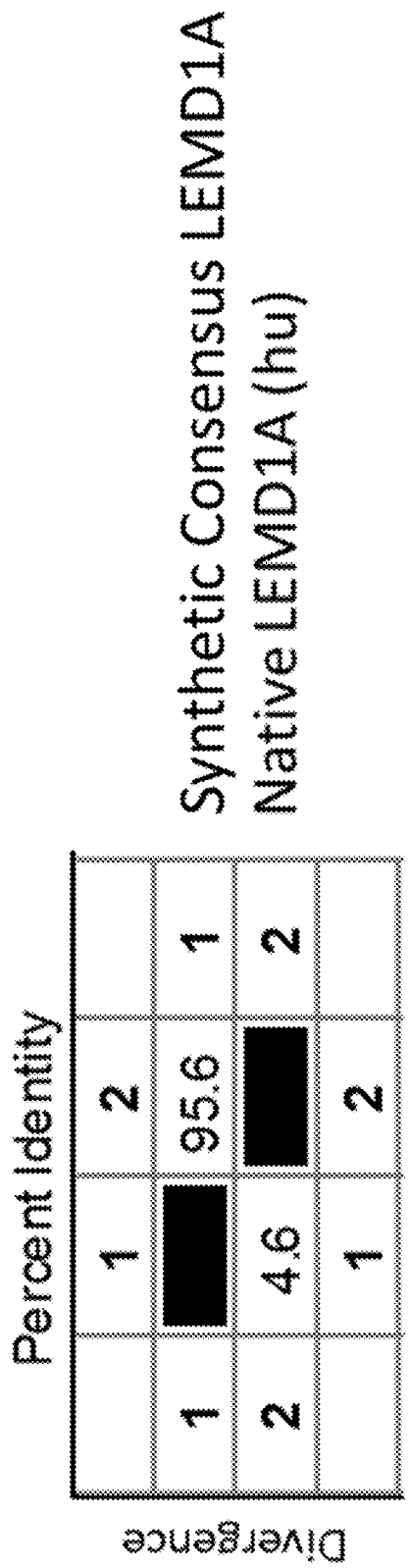
FIG. 1A is a sequence alignment of amino acids 19-198 of synthetic consensus LEMD1A (SEQ ID NO: 13) with native human LEMD1A (SEQ ID NO: 14).
FIG. 1B presents the sequence identity and divergence between native and synthetic consensus LEMD1A.

The present invention relates to a vaccine comprising a LEMD1 antigen. LEMD1 is expressed in many tumors. Accordingly, the vaccine provides treatment for a cancer or cancer-based tumor expressing LEMD1. The vaccine of the invention can provide any combination of particular cancer antigens for the particular prevention or treatment of the cancer of a subject that is in need of treatment.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The aforementioned approaches can be combined so that the final recombinant cancer antigen has a percent similarity to native cancer antigen amino acid sequence as discussed above.

The LEMD1 antigen can be a consensus LEMD1 antigen derived from the sequences of LEMD1 from different species or from different isoforms within a species, and thus, the consensus LEMD1 antigen is non-native. The recombinant LEMD1 can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, by designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B-cell responses.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening value having the same degree of precision as the recited range minimum and maximum is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described herein.

"Antibody" as used herein means an antibody of classes IgG, IgM, IgA, IgD, or IgE, or fragments, or derivatives thereof, including Fab, F(ab')2, Fd, and single chain antibodies, diabodies, bispecific antibodies, bifunctional antibodies, and derivatives thereof. The antibody can be an antibody isolated from the serum sample of a mammal, a polyclonal antibody, an affinity purified antibody, or any mixture thereof, which exhibits sufficient binding specificity to a desired epitope or a sequence derived therefrom.

"Antigen" refers to proteins having mutated LEMD1 amino acid sequences including SEQ ID NO: 2 and fragments thereof of lengths set forth herein such as amino acid residues 19 to 198 of SEQ ID NO:2; variants, i.e. proteins with sequences having identity to SEQ ID NO: 2, as set forth herein and fragments of variants having lengths set forth herein, and combinations thereof "Antigen" also refers to proteins having mutated LEMD1 amino acid sequences including SEQ ID NO: 4 and fragments thereof of lengths set forth herein such as amino acid residues 19 to 84 of SEQ ID NO:4; variants, i.e. proteins with sequences having identity to SEQ ID NO: 4 as set forth herein and fragments of variants having lengths set forth herein, and combinations thereof "Antigen" also refers to proteins having mutated LEMD1 amino acid sequences including SEQ ID NO: 6 and fragments thereof of lengths set forth herein such as amino acid residues 19 to 198 and 206 to 271 of SEQ ID NO:6; variants, i.e. proteins with sequences having identity to SEQ ID NO: 6 as set forth herein and fragments of variants having lengths set forth herein, SEQ ID NO: 6, and combinations thereof. Antigens may optionally include signal peptides such as those from other proteins.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of a subject or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Constant current" as used herein describes a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below, excluding an heterologous signal peptide added. The fragment may comprise at least 95%, at least 96%, at least 97%, at least 98%, or at least 99% of one or more of the nucleic acid sequences set forth below and additionally optionally comprise sequence encoding a heterologous signal peptide which is not included when calculating percent identity. Fragments may further comprise coding sequences for a signal peptide such as an immunoglobulin signal peptide, for example an IgE or IgG signal peptide. The coding sequence encoding an N terminal methionine and/or signal peptide may be linked to a fragment of coding sequence.

In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein, excluding any heterologous signal peptide added. The fragment may comprise at least 95%, at least 96%, at least 97%, at least 98%, or at least 99% of one or more of the amino sequences set forth below and additionally optionally comprise a heterologous signal peptide which is not included when calculating percent identity. Fragments may further comprise a signal peptide such as an immunoglobulin signal peptide, for example an IgE or IgG signal peptide.

In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, at least 240 amino acids or more, at least 250 amino acids or more, or at least 260 amino acids or more of a protein sequence disclosed herein.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in the cells of the subject to whom the nucleic acid molecule is administered. As used herein, the term "expressible form" refers to a gene construct that contain the necessary regulatory elements operably linked to a coding sequence that encodes a protein such that, when present in cell of a subject, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule which is capable of conferring, activating, or enhancing expression of a nucleic acid in a cell. A promoter can comprise one or more specific transcriptional regulatory sequences to further enhance expression and/or to alter the spatial expression and/or temporal expression of a nucleic acid in a cell. A promoter can also comprise distal enhancer or repressor elements, which can be located as much as several thousand base pairs from the start site of transcription. A promoter can be derived from sources including viral, bacterial, fungal, plant, insect, and animal. A promoter can regulate the expression of a gene component constitutively or differentially with respect to cell, tissue, or organ in which expression occurs, or with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treat," "treatment," or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" as used herein with respect to a peptide or polypeptide means a peptide or polypeptide that differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

Vaccine

Provided herein are vaccines comprising a LEMD1 antigen or a nucleic acid encoding a LEMD1 antigen as described herein. In some embodiments, the vaccines comprise one or more nucleic acid molecules that encode a LEMD1 antigen as described herein. In some embodiments, the vaccines comprise one or more nucleic acid molecules that comprise a nucleic acid sequence that encodes amino acids. In some embodiments, the one or more nucleic acid molecules encodes an antigen. In some embodiments, the nucleic acid molecule comprises one or more nucleic acid sequences selected from the group consisting of (a) nucleotides 55 to 600 of SEQ ID NO: 1; (b) nucleotides 55 to 258 of SEQ ID NO: 3; (c) nucleotides 55 to 594 and 616 to 819 of SEQ ID NO: 5; (d) a fragment comprising at least 90% of an entire length a nucleic acid molecule comprising nucleotides 55 to 600 of SEQ ID NO: 1; (e) a fragment comprising at least 90% of an entire length a nucleic acid molecule comprising nucleotides 55 to 258 of SEQ ID NO: 3; (f) a fragment comprising at least 90% of an entire length a nucleic acid molecule comprising nucleotides 55 to 594 and 616 to 819 of SEQ ID NO: 5; (g) a fragment that is at least 95% identical to nucleotides 55 to 600 of SEQ ID NO: 1; (h) a fragment that is at least 95% identical to nucleotides 55 to 258 of SEQ ID NO: 3; (i) a fragment that is at least 95% identical to nucleotides 55 to 594 and 616 to 819 of SEQ ID NO: 5; (j) a fragment comprising at least 90% of an entire length of a nucleic acid sequence that is at least 95% identical to nucleotides 55 to 600 of SEQ ID NO: 1; (k) a fragment comprising at least 90% of an entire length of a nucleic acid sequence that is at least 95% identical to nucleotides 55 to 258 of SEQ ID NO: 3; and (1) a fragment comprising at least 90% of an entire length of a nucleic acid sequence that is at least 95% identical to nucleotides 55 to 594 and 616 to 819 of SEQ ID NO: 1. In some embodiments of the present invention, the nucleic acid molecule encodes proteins and peptides comprising the amino acid sequence selected from the group consisting of (a) amino acid residues 19 to 198 of SEQ ID NO: 2; (b) amino acid residues 19 to 84 of SEQ ID NO: 4; (c) amino acid residues 19 to 198 and 206 to 271 of SEQ ID NO: 6; (d) a fragment comprising at least 90% of an entire length of amino acid residues 19 to 198 of SEQ ID NO: 2; (e) a fragment comprising at least 90% of an entire length of amino acid residues 19 to 84 of SEQ ID NO: 4; (f) a fragment comprising at least 90% of an entire length of amino acid residues 19 to 198 and 206 to 271 SEQ ID NO: 6; (g) an amino acid sequence that is greater than 95.6% identical to amino acid residues 19 to 198 of SEQ ID NO: 2; (h) an amino acid sequence that is greater than 95.5% identical to amino acid residues 19 to 84 of SEQ ID NO: 4; (i) an amino acid sequence that is at least 95% identical to amino acid residues 19 to 198 and 206 to 271 of SEQ ID NO: 6; (j) a fragment comprising at least 90% of an entire length of an amino acid sequence that is greater than 95.6% identical to amino acid sequences 19 to 198 of SEQ ID NO: 2; (k) a fragment comprising at least 90% of an entire length of an amino acid sequence that is greater than 95.5% identical to amino acid sequences 19 to 84 of SEQ ID NO: 4; and (1) a fragment comprising at least 90% of an entire length of an amino acid sequence that is at least 95% identical to amino acid sequences 19 to 198 and 206 and 271 of SEQ ID NO: 6.

In some aspects of the present disclosure, the vaccine comprises an antigen, wherein the antigen comprises the amino acid sequence selected from the group consisting of (a) amino acid residues 19 to 198 of SEQ ID NO: 2; (b) amino acid residues 19 to 84 of SEQ ID NO: 4; (c) amino acid residues 19 to 198 and 206 to 271 of SEQ ID NO: 6; (d) a fragment comprising at least 90% of an entire length of amino acid residues 19 to 198 of SEQ ID NO: 2; (e) a fragment comprising at least 90% of an entire length of amino acid residues 19 to 84 of SEQ ID NO: 4; (f) a fragment comprising at least 90% of an entire length of amino acid residues 19 to 198 and 206 to 271 SEQ ID NO: 6; (g) an amino acid sequence that is greater than 95.6% identical to amino acid residues 19 to 198 of SEQ ID NO: 2; (h) an amino acid sequence that is greater than 95.5% identical to amino acid residues 19 to 84 of SEQ ID NO: 4; (i) an amino acid sequence that is at least 95% identical to amino acid residues 19 to 198 and 206 to 271 of SEQ ID NO: 6; (j) a fragment comprising at least 90% of an entire length of an amino acid sequence that is greater than 95.6% identical to amino acid sequences 19 to 198 of SEQ ID NO: 2; (k) a fragment comprising at least 90% of an entire length of an amino acid sequence that is greater than 95.5% identical to amino acid sequences 19 to 84 of SEQ ID NO: 4; and (1) a fragment comprising at least 90% of an entire length of an amino acid sequence that is at least 95% identical to amino acid sequences 19 to 198 and 206 and 271 of SEQ ID NO: 6.

In some aspects of the present disclosure the vaccine comprises a nucleic acid molecule, wherein the nucleic acid molecule comprises a nucleic acid sequence having at least about 95% identity over an entire length of the nucleic acid sequence set forth in SEQ ID NO: 1, 3, or 5. In some aspects, the vaccine comprises a nucleic acid molecule, wherein the nucleic acid molecule encodes a peptide comprising an amino acid sequence having at least about 95.6%, 95.5%, or 95% identity over an entire length of the amino acid sequence set forth in SEQ ID NO: 2, 4, or 6, respectively.

In some embodiments of the present invention the nucleic acid molecule present in the vaccine comprises an expression vector. In some embodiments, the vaccine further comprises a pharmaceutically acceptable excipient, and in some embodiments the vaccine further comprises an adjuvant, which in some aspects of the embodiment can be IL-12, IL-15, IL-28, or RANTES.

In some embodiments, the vaccine comprises a peptide, wherein the peptide comprises an amino acid sequence having at least about 95.6%, 95.5%, or 95% identity over an entire length of the amino acid sequence set forth in SEQ ID NO: 2, 4, or 6, respectively. In other embodiments, the vaccine comprises a peptide, wherein the peptide comprises the amino acid sequence set forth in SEQ ID NO: 2, 4, or 6.

The vaccines can be capable of generating in a subject an immune response against the antigen. The immune response can be a therapeutic or prophylactic immune response.

The vaccines can be used to protect against cancer, for example, a cancer or tumor expressing LEMD1. The vaccines can be used to prevent and/or treat a tumor expressing LEMD1 in a subject in need thereof. The vaccines can induce cellular and/or antibody responses against LEMD1 and against tumors expressing LEMD1.

The development of a cancer vaccine as described herein comprises identifying a cancer antigen, e.g., LEMD1, that is not recognized by the immune system and is a self-antigen.

The cancer antigen identified is changed from a self-antigen to a foreign antigen in order to be recognized by the immune system. The redesign of the nucleic acid and amino acid sequence of the recombinant cancer antigen from a self to a foreign antigen breaks tolerance of the antigen by the immune system. In order to break tolerance, several redesign measures can be applied to the cancer antigen as described below.

The recombinant cancer antigen of the vaccine is not recognized as self, thereby breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine can increase tumor free survival by 30%, 31%, 32%, 33%, 34%, 35%, 36%, 37%, 38%, 39%, 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in a subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in a subject not administered the vaccine.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more cancer antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

In some embodiments, the vaccine may further comprise a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). In some embodiments, the nucleic acid vaccine may further comprise coding sequence for a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, IL-31, IL-33 and/or RANTES may be included on one or more nucleic acid molecules that comprise coding sequence for one or more antigens. Coding sequence for IL-12, IL-15, IL-28, IL-31, IL-33 and/or RANTES may be included on a separate nucleic acid molecules such as a separate plasmid.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the cancer antigen as discussed below.

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

Antigen

As described above, the vaccine can comprise a LEMD1 antigen or a nucleic acid molecule encoding a LEMD1 antigen. The antigen can be LEMD1, a fragment thereof, a variant thereof, or a combination thereof.

The vaccine can be used for treating subjects suffering from LEMD1-expressing cancer. The vaccine can also be used for treating subjects with cancers or tumors that express LEMD1 or preventing development of such tumors in subjects. The LEMD1 antigen can differ from the native, "normal" LEMD1 gene, and thus provide therapy or prophylaxis against an LEMD1 antigen-expressing tumor. Accordingly, LEMD1 antigen sequences that differ from the native LEMD1 gene (i.e., mutated LEMD1 genes or sequences) are provided herein. For example, some aspects of the present disclosure provide for vaccine comprising a nucleic acid molecule comprising the nucleic acid sequence set forth in SEQ ID NO: 1, 3, or 5, and some aspects provide for a vaccine comprising a nucleic acid molecule comprising a nucleic acid sequence that encodes the amino acid sequence set forth in SEQ ID NO: 2, 4 or 6. In some aspects of the vaccine comprising a nucleic acid molecule, the nucleic acid molecule comprises one or more nucleic acid sequences selected from the group consisting of (a) nucleotides 55 to 600 of SEQ ID NO: 1; (b) nucleotides 55 to 258 of SEQ ID NO: 3; (c) nucleotides 55 to 594 and 616 to 819 of SEQ ID NO: 5; (d) a fragment comprising at least 90% of an entire length a nucleic acid molecule comprising nucleotides 55 to 600 of SEQ ID NO: 1; (e) a fragment comprising at least 90% of an entire length a nucleic acid molecule comprising nucleotides 55 to 258 of SEQ ID NO: 3; (f) a fragment comprising at least 90% of an entire length a nucleic acid molecule comprising nucleotides 55 to 594 and 616 to 819 of SEQ ID NO: 5; (g) a fragment that is at least 95% identical to nucleotides 55 to 600 of SEQ ID NO: 1; (h) a fragment that is at least 95% identical to nucleotides 55 to 258 of SEQ ID NO: 3; (i) a fragment that is at least 95% identical to nucleotides 55 to 594 and 616 to 819 of SEQ ID NO: 5; (j) a fragment comprising at least 90% of an entire length of a nucleic acid sequence that is at least 95% identical to nucleotides 55 to 600 of SEQ ID NO: 1; (k) a fragment comprising at least 90% of an entire length of a nucleic acid sequence that is at least 95% identical to nucleotides 55 to 258 of SEQ ID NO: 3; and (1) a fragment comprising at least 90% of an entire length of a nucleic acid sequence that is at least 95% identical to nucleotides 55 to 594 and 616 to 819 of SEQ ID NO: 1.

Isolated nucleic acid molecules comprising the above-described heterologous sequences are provided. Isolated nucleic acid molecules consisting of the above-described heterologous sequences are provided. Isolated nucleic acid molecules comprising the above-described heterologous sequences may be incorporated into vectors such as plasmids, viral vectors and other forms of nucleic acid molecules as described below. Provided herein are nucleic acid sequences that encode LEMD1 antigens. Coding sequences encoding LEMD1 antigens have the sequences as described above.

Protein molecules comprising the above-described heterologous amino acid sequences are provided. Protein molecules consisting of above described heterologous amino acid sequences are provided. Provided herein are proteins and polypeptides having the above-described sequences. Some embodiments of the present disclosure provide a protein comprising the amino acid sequence selected from the group consisting of (a) amino acid residues 19 to 198 of SEQ ID NO: 2; (b) amino acid residues 19 to 84 of SEQ ID NO: 4; (c) amino acid residues 19 to 198 and 206 to 271 of SEQ ID NO: 6; (d) a fragment comprising at least 90% of an entire length of amino acid residues 19 to 198 of SEQ ID NO: 2; (e) a fragment comprising at least 90% of an entire length of amino acid residues 19 to 84 of SEQ ID NO: 4; (f) a fragment comprising at least 90% of an entire length of amino acid residues 19 to 198 and 206 to 271 SEQ ID NO: 6; (g) an amino acid sequence that is greater than 95.6% identical to amino acid residues 19 to 198 of SEQ ID NO: 2; (h) an amino acid sequence that is greater than 95.5% identical to amino acid residues 19 to 84 of SEQ ID NO: 4; (i) an amino acid sequence that is at least 95% identical to amino acid residues 19 to 198 and 206 to 271 of SEQ ID NO: 6; (j) a fragment comprising at least 90% of an entire length of an amino acid sequence that is greater than 95.6% identical to amino acid sequences 19 to 198 of SEQ ID NO: 2; (k) a fragment comprising at least 90% of an entire length of an amino acid sequence that is greater than 95.5% identical to amino acid sequences 19 to 84 of SEQ ID NO: 4; and (1) a fragment comprising at least 90% of an entire length of an amino acid sequence that is at least 95% identical to amino acid sequences 19 to 198 and 206 and 271 of SEQ ID NO: 6.

The proteins and polypeptides may be referred to as LEMD1 antigens and LEMD1 immunogens. LEMD1 antigens are capable of eliciting an immune response against cancer cells and tumors expressing a LEMD1 antigen.

In one aspect of the invention, it is desired that the consensus antigen provides for improved transcription and translation, including having one or more of the following: low GC content leader sequence to increase transcription; mRNA stability and codon optimization and eliminating to the extent possible cis-acting sequence motifs (i.e., internal TATA-boxes).

In some aspects of the invention, it is desired to generate a consensus antigen that generates a broad immune response across multiple strains, including having one or more of the following: incorporate all available full-length sequences; computer generated sequences that utilize the most commonly occurring amino acid at each position; and increase cross-reactivity between strains.

The LEMD1 antigen can be a consensus antigen (or immunogen) sequence derived from two or more species. The LEMD1 antigen can comprise a consensus sequence and/or modification(s) for improved expression. Modification can include codon optimization, RNA optimization, addition of a kozak sequence (e.g., GCC ACC) for increased translation initiation and/or the addition of an immunoglobulin leader sequence to increase the immunogenicity of the LEMD1 antigen. The LEMD1 antigen can comprise a signal peptide such as an immunoglobulin signal peptide, for example, but not limited to, an immunoglobulin E (IgE) or immunoglobulin G (IgG) signal peptide. In some embodiments, the LEMD1 consensus antigen can comprise a hemagglutinin (HA) tag. The LEMD1 consensus antigen can be designed to elicit stronger and broader cellular and/or humoral immune responses than a corresponding codon optimized LEMD1 antigen.

The LEMD1 consensus antigen can comprise one or more mutations, thereby eliciting stronger and broader cellular and/or humoral immune responses than a corresponding codon optimized LEMD1 antigen.

The LEMD1 consensus antigen can be nucleotides 55 to 600 of the nucleic acid SEQ ID NO: 1, which encodes amino acid residues 19 to 198 of SEQ ID NO: 2. In some embodiments, the LEMD1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO: 1. In other embodiments, the LEMD1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO: 2.

The LEMD1 consensus antigen can be nucleotides 55 to 258 of the nucleic acid SEQ ID NO: 3, which encodes amino acid residues 19 to 84 of SEQ ID NO: 4. In some embodiments, the LEMD1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO: 3. In other embodiments, the LEMD1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO: 4.

The LEMD1 consensus antigen can be nucleotides 55 to 594 and 616 to 819 of the nucleic acid SEQ ID NO: 5, which encodes amino acid residues 19 to 198 and 206 to 271 of SEQ ID NO: 6. In some embodiments, the LEMD1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO: 5. In other embodiments, the LEMD1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO: 6.

The LEMD1 antigen can comprise modifications for improved expression. Modification can include codon optimization, RNA optimization, addition of a kozak sequence (e.g., GCC ACC) for increased translation initiation and/or the addition of an immunoglobulin leader sequence to increase the immunogenicity of the antigen. The LEMD1 antigen can comprise a signal peptide such as an immunoglobulin signal peptide, for example, but not limited to, an immunoglobulin E (IgE) or immunoglobulin G (IgG) signal peptide.

The LEMD1 antigen can comprise modifications for epitope optimization. In some embodiments, a cleavage site such may be inserted between multiple LEMD1 antigen sequences. The cleavage site may be a furin cleavage site.

Vaccine in Combination with Immune Checkpoint Inhibitor

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune checkpoint inhibitor can be an antibody, a variant thereof, a fragment thereof, or a combination thereof.

1. Immune Checkpoint Molecule

The immune checkpoint molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

a. PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is upregulated on macrophages and dendritic cells (DCs) in response to LPS and GM-CSF treatment and onn T cells and B cells upon TCR and B cell receptor signaling. PD-L1 is expressed by many tumor cell lines, including myelomas, mastocytomas, and melanomas.

2. Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the $F(ab')_2$ fragment, which comprises both antigen-binding sites. Accordingly, the antibody can be the Fab or $F(ab')_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

a. PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

b. PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

Vector

The vaccine can comprise one or more vectors that include a heterologous nucleic acid encoding the LEMD1 antigen. The one or more vectors can be capable of expressing the antigen in a quantity effective to elicit an immune response in the mammal. The vector may comprise heterologous nucleic acid encoding the antigen. The vector can have a nucleic acid sequence containing an origin of replication. The vector can be a plasmid, bacteriophage, bacterial artificial chromosome, or yeast artificial chromosome. The vector can be either a self-replication extra chromosomal vector, or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

The vectors may comprise nucleic acid sequences operably linked to a regulatory element selected from a promoter and a poly-adenylation signal. In some embodiments, the promoter is a human cytomegalovirus immediate-early promoter (hCMV promoter). In some embodiments, the poly-adenylation signal is a bovine growth hormone poly-adenylation signal (bGH polyA).

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development. The vector can be a plasmid. The plasmid may be useful for transfecting cells with nucleic acid encoding the antigen, which the transformed host cells is cultured and maintained under conditions wherein expression of the antigen takes place.

The plasmid may comprise a nucleic acid sequence that encodes one or more of the various antigens disclosed above including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants consensus proteins.

A single plasmid may contain coding sequence for a single antigen, coding sequence for two antigens, coding sequence for three antigens or coding sequence for four antigens. In some embodiments, a plasmid may further comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be p V AXI, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pA V0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5" of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells. The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system. The LEC can be pcrM2. The LEC can be perNP. perNP and pcrMR can be derived from pNP (Puerto Rico/34) and pM2 (New Caledonia/99), respectively.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Methods of Preparing the Vector

Provided herein are methods for preparing the vector that comprise the nucleic acid molecule encoding LEMD1 antigen discussed herein. The vector, after the final subcloning step into the mammalian expression plasmid, can be used to inoculate a cell culture in a large scale fermentation tank, using known methods in the art.

The vector for use with the EP devices, which are described below in more detail, can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Excipients and Other Components of the Vaccine

The vaccine may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative plasmid or are delivered as proteins in combination with the plasmid above in the vaccine. The one or more adjuvants may be selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1~, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/USI0/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-t, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may comprise the antigen and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of DNA. In some preferred embodiments, vaccine can contain about 10 nanograms to about 800 micrograms of DNA. In some preferred embodiments, the vaccine can contain about 0.1 to about 500 micrograms of DNA. In some preferred embodiments, the vaccine can contain about 1 to about 350 micrograms of DNA. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid thereof.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Pharmaceutical Compositions of the Vaccine

The vaccine can be in the form of a pharmaceutical composition. The pharmaceutical composition can comprise the vaccine. The pharmaceutical compositions can comprise about 5 nanograms (ng) to about 10 milligrams (mg) of the DNA of the vaccine. In some embodiments, pharmaceutical compositions according to the present invention comprise about 25 ng to about 5 mg of DNA of the vaccine. In some embodiments, the pharmaceutical compositions contain about 50 ng to about 1 mg of DNA of the vaccine. In some embodiments, the pharmaceutical compositions contain about 0.1 to about 500 micrograms of DNA of the vaccine. In some embodiments, the pharmaceutical compositions contain about 1 to about 350 micrograms of DNA of the vaccine. In some embodiments, the pharmaceutical compositions contain about 5 to about 250 micrograms of DNA of the vaccine. In some embodiments, the pharmaceutical compositions contain about 10 to about 200 micrograms of DNA of the vaccine. In some embodiments, the pharmaceutical compositions contain about 15 to about 150 micrograms of DNA of the vaccine. In some embodiments, the pharmaceutical compositions contain about 20 to about 100 micrograms of DNA of the vaccine. In some embodiments, the pharmaceutical compositions contain about 25 to about 75 micrograms of DNA of the vaccine. In some embodiments, the pharmaceutical compositions contain about 30 to about 50 micrograms of DNA of the vaccine. In some embodiments, the pharmaceutical compositions contain about 35 to about 40 micrograms of DNA of the vaccine. In some embodiments, the pharmaceutical compositions contain about 100 to about 200 micrograms of DNA of the vaccine. In some embodiments, the pharmaceutical compositions comprise about 10 micrograms to about 100 micrograms of DNA of the vaccine. In some embodiments, the pharmaceutical compositions comprise about 20 micrograms to about 80 micrograms of DNA of the vaccine. In some embodiments, the pharmaceutical compositions comprise about 25 micrograms to about 60 micrograms of DNA of the vaccine. In some embodiments, the pharmaceutical compositions comprise about 30 ng to about 50 micrograms of DNA of the vaccine. In some embodiments, the pharmaceutical compositions comprise about 35 ng to about 45 micrograms of DNA of the vaccine. In some preferred embodiments, the pharmaceutical compositions contain about 0.1 to about 500 micrograms of DNA of the vaccine. In some preferred embodiments, the pharmaceutical compositions contain about 1 to about 350 micrograms of DNA of the vaccine. In some preferred embodiments, the pharmaceutical compositions contain about 25 to about 250 micrograms of DNA of the vaccine. In some preferred embodiments, the pharmaceutical compositions contain about 100 to about 200 micrograms of DNA of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 ng of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 ng of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules such as vehicles, adjuvants, carriers, or diluents. The pharmaceutically acceptable excipient can be a transfection facilitating agent.

In some embodiments, the transfection facilitating agent is a polyanion, polycation, including poly-L-glutamate (LGS), or lipid. In one embodiment, the transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the transfection facilitating agent can comprise lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Concentration of the transfection agent in the vaccine can be less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in one or more alternative plasmids or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

Methods of Vaccination

Provided herein are methods for treating and/or preventing LEMD1-expressing cancer using the pharmaceutical formulations described above. Also described herein are methods of using the pharmaceutical formulations described above in the treatment and/or prevention of cancer in a subject. Also described herein are methods of vaccinating a subject. Also described herein are methods of administering the pharmaceutical formulations described herein to a subject in need thereof. The methods described herein collectively referred to as methods of treatment using the pharmaceutical formulations described herein can comprise administering one or more vaccine as described herein to a subject in need thereof to induce a therapeutic and/or prophylactic immune response. The vaccine can be administered to a subject to modulate the activity of the subject's immune system and enhance the immune response. The administration of the vaccine can be the transfection of the cancer antigens as disclosed herein as a nucleic acid molecule that is expressed in the cell and delivered to the surface of the cell, whereupon the immune system recognizes and induces a cellular, humoral, or cellular and humoral response. The administration of the vaccine can be used to induce or elicit an immune response in subjects against one or more of the cancer antigens as disclosed herein by administering to the subject the vaccine as discussed herein.

The vaccine can be administered to a subject to modulate the activity of the subject's immune system, thereby enhancing the immune response. In some embodiments, the subject is a mammal. Upon administration of the vaccine to the mammal, and thereby introducing the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, and preferably human, cow, or pig. The vaccine can likewise be administered to a non-mammal subject, for example, a chicken, to elicit an immune response.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Methods of Generating an Immune Response with the Vaccine

The vaccine can be used to generate an immune response in a mammal or non-mammal subject, including therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which embodiments comprise administering the vaccine to a subject. Some embodiments provide methods of prophylactically vaccinating a subject against a cancer or tumor expressing one or more of the cancer antigens as described above, which embodiments comprise administering the vaccine. Some embodiments provide methods of therapeutically vaccinating a subject that has been suffering from the cancer or tumor expressing one or more of the cancer antigens, which embodiments comprise administering the vaccine. Diagnosis of the cancer or tumor expressing the one or more cancer antigens as disclosed herein prior to administration of the vaccine can be done routinely.

Methods of Cancer Treatment with the Vaccine

The vaccine can be used to generate or elicit an immune response in a mammal that is reactive or directed to a cancer or tumor (e.g., HPV-mediated cancers, epithelial ovarian cancer, melanoma, head and neck cancer, cervical cancer, liver cancer, prostate cancer, blood cancers, esophageal squamous cell carcinomas, gastric cancer) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine. The treated cancer or tumor based growth can be any type of cancer such as, but not limited to, colorectal cancer.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8$^+$ (CTL) to attack and kill tumor cells; (3) increase T helper cell responses; (4) and increase inflammatory responses via IFN-γ and TFN-α or preferably all of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase survival, reduce tumor mass, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject after immunization. The administered vaccine can prevent and block LEMD1-mediated tumorigenesis and/or tumor progression as compared to a cellular immune response in a subject not administered the vaccine. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to a cellular immune response in a subject not administered the vaccine.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to a cellular immune response in a subject not administered the vaccine.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Routes of Administration

The vaccine or pharmaceutical composition can be administered by different routes including orally, parenterally, sublingually, transdermally, rectally, transmucosally, topically, via inhalation, via buccal administration, intrapleurally, intravenously, intraarterially, intraperitoneally, subcutaneously, intramuscularly, intranasal intrathecally, and/or intraarticularly, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administered to the mammal by several well-known technologies including DNA injection (also referred to as DNA vaccination) with and without in vivo electroporation, liposome mediated transfection, nanoparticle facilitated transfection, and use recombinant vectors such as recombinant adenovirus, recombinant adenovirus associated virus, and recombinant vaccinia. The one or more cancer antigens of the vaccine can be administered via DNA injection along with in vivo electroporation.

Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferably the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate administration of the DNA vaccines of the present invention include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deneurological system the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

Method of Preparing the Vaccine

Provided herein are methods for preparing the DNA plasmids that comprise the vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Consensus LEMD1

Consensus LEMD1A

In order to generate a human consensus LEMD1A, eight LEMD1A sequences were collected from GenBank (www.ncbi.nlm.nih.gov/genbank). The GenBank accession numbers for selected sequences are: NP_001185979.1; XP_003938379.1; XP_012314760.1; XP_002760754.2; XP_012513307.1; XP_011371293.1; XP_011221935.1; and XP_007086602.1.

A consensus sequence was generated using the DNASTAR® Lasergene software package (version 13.0.0.357). The eight sequences listed above were imported into MegAlign and aligned using the ClustalW multiple sequence alignment program. The resulting LEMD1A sequence shares 97.2% identity with human native LEMD1A.

Consensus LEMD1F

In order to generate a human consensus LEMD1F, six LEMD1F sequences were collected from GenBank (www.ncbi.nlm.nih.gov/genbank). The GenBank accession numbers for selected sequences are: NP_001185981.1; XP_011845800.1; XP_011813129.1; XP_010347273.1; XP_012314764.1; and XP_012513311.1.

A consensus sequence was generated using the DNASTAR® Lasergene software package (version 13.0.0.357). The six sequences listed above were imported into MegAlign and aligned using the ClustalW multiple sequence alignment program. The resulting LEMD1F sequence shares 98.5% identity with human native LEMD1F.

Example 2

Synthetic Consensus LEMD1A

Abolishing Biological Function of LEMD1A

In order to abolish the potential biological function of the resulting consensus LEMD1A, three mutations in the LEM domain (G20A, P25A and Y34A) were introduced to disrupt BAF binding. As a result, the synthetic consensus LEMD1A protein shares 95.6% identity with native human LEMD1A protein as shown in FIGS. 1A and 1B.

Optimizing Expression

Figure 2:
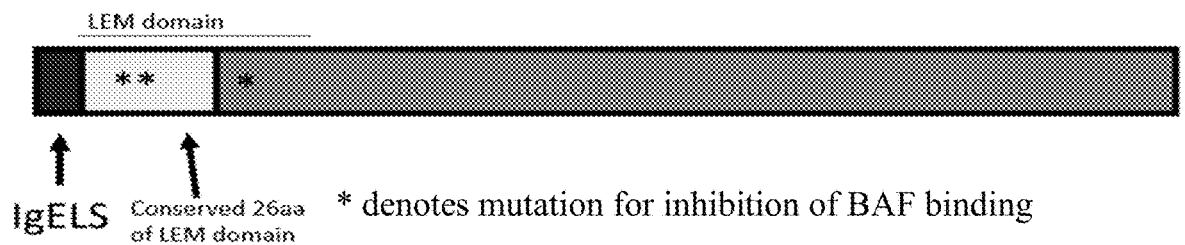
FIG. 2 is a schematic representation of synthetic consensus LEMD1A.

Once the synthetic consensus LEMD1A DNA sequence was obtained, in order to have a higher level of expression, the N-terminal methionine of the synthetic consensus LEMD1A was removed and an upstream Kozak sequence and IgE leader were added to the N-terminus. Furthermore, the codon usage of this gene was adapted to the codon bias of *Homo sapiens* genes, and RNA optimization was also performed with regions of very high (>80%) or very low (<30%) GC content, cis-acting sequence motifs such as internal TATA boxes, chi-sites and ribosomal entry sites being avoided. A schematic representation of synthetic consensus LEMD1A is presented in FIG. 2. Characteristics of the synthetic consensus LEMD1A are provided in Table 1.

TABLE 1

Characteristics of synthetic consensus LEMD1A

| Characteristics | Synthetic Consensus LEMD1A |
|---|---|
| Identity to native human LEMD1A | 95.6% |
| Identity to native rhesus LEMD1A | 56.2-92.8% |
| Identity to native mouse LEMD1A | 32.2-60.6% |
| Number of amino acid mutations (vs native human) | 8 |
| Number of inserted mutations (not consensus derived) | 3 |
| Molecular weight | 200 aa (22 kDa) |
| Length of coding sequence (bp) | 600 |

Figure 3:
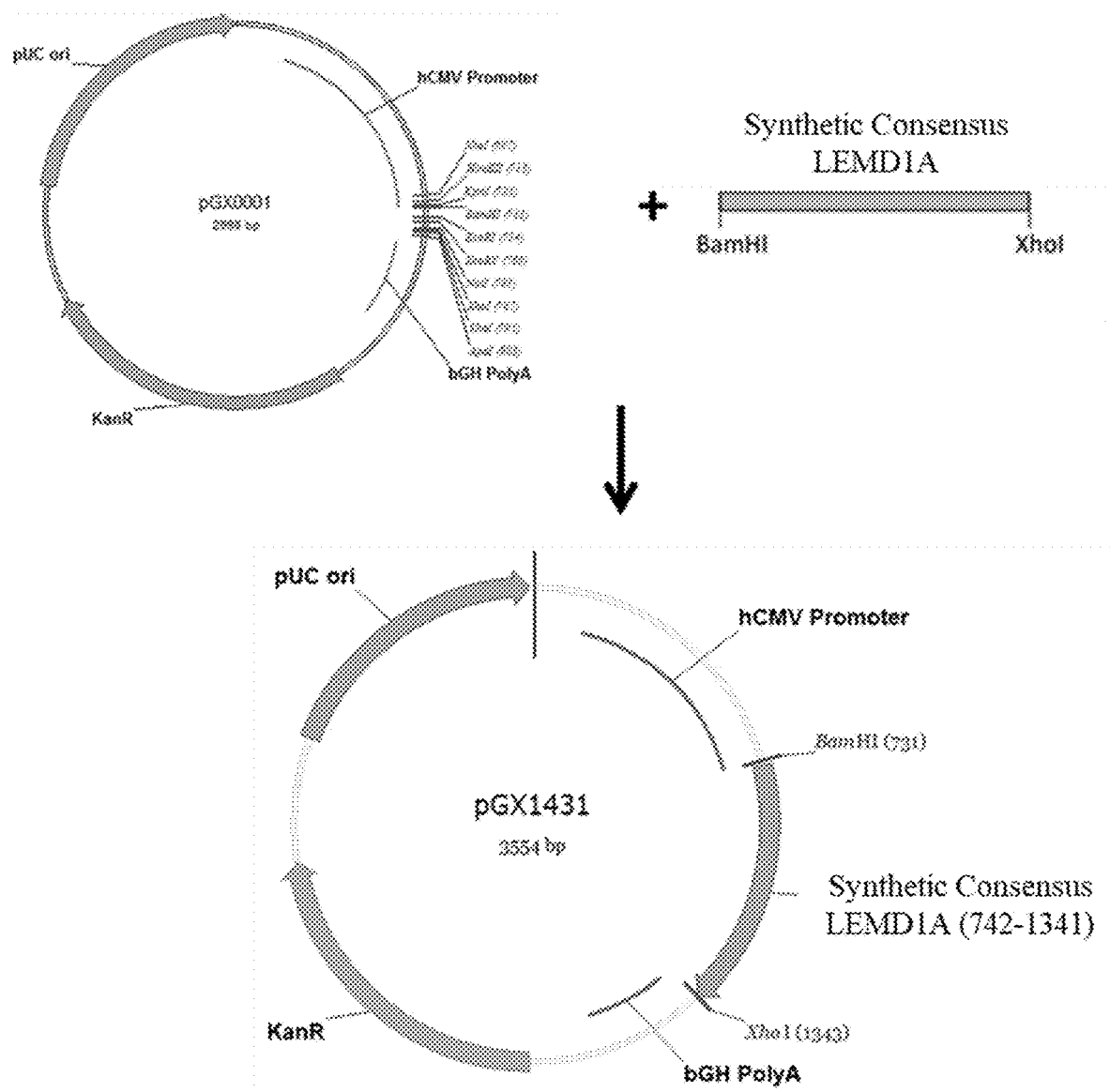
FIG. 3 illustrates the cloning strategy employed to generate pGX1431.

Referring to FIG. 3, the synthesized synthetic consensus LEMD1A was digested with BamHI and XhoI, and cloned into expression vector pGX0001 (Inovio Pharmaceuticals). The pGX0001 backbone is a modified pVAX1 expression vector under the control of the human cytomegalovirus immediate-early promoter (hCMV promoter). Modifications were introduced into pVAX1 to create pGX0001 and are identified based on the reported sequence of pVAX1 available from ThermoFisher Scientific. These modifications are listed in Table 2.

TABLE 2

| Variant | Nucleotide | Description |
|---|---|---|
| ACT > CTG | 2, 3, 4 | upstream of CMV promoter. |
| C > G | 241 | in CMV promoter |
| C > T | 1158 | backbone, downstream of the bovine growth hormone polyadenylation signal (bGH polyA) |
| A>— | 2092 | backbone, downstream of the Kanamycin resistance gene |
| C > T | 2493 | in pUC origin of replication (pUC ori) |
| G > C | 2969 | in very end of pUC Ori upstream of RNASeH site |

The pGX0001 backbone includes the kanamycin resistance gene (KanR) and plasmid origin of replication (pUC ori) for production purpose. Those elements are not functional in eukaryotic cells. Elements present in the 2998 base pair pGX0001 include the following:
  CMV promoter: bases 137-724
  T7 promoter/priming site: bases 664-683
  Multiple cloning site: bases 696-811
  Bovine GH polyadenylation signal: bases 829-1053
  Kanamycin resistance gene: bases 1226-2020
  pUC origin: bases 2319-2992

The plasmid resulting from cloning LEMD1A into the pGX0001 backbone was designated pGX1431, and the full length sequence was confirmed to be correct. pGX1431 is a DNA plasmid encoding the synthetic consensus LEMD1A protein. Related mRNA production is driven by a human CMV promoter (hCMV promoter) and terminated by the bovine growth hormone 3' end poly-adenylation signal (bGH polyA). Features of pGX1431 are presented in Table 3.

TABLE 3

| Elements: | Base Pairs: |
|---|---|
| hCMV Promoter: | 137-724 |
| Synthetic Consensus LEMD1A Coding Sequence: | 742-1341 |
| bGH PolyA: | 1385-1609 |
| Kanamycin Resistance (KanR): | 1782-2576 |
| pUC Ori: | 2875-3548 |

```
Amino acid insert sequence of pGX1431
                                                      (SEQ ID NO: 2)
  1 MDWTWILFLV AAATRVHSVD VKCLSDCKLQ NQLEKLAFSP GAILPSTRKL

51 AEKKLVQLLV SPPCAPPVMN GPRELDGAQD SDDSEELNII LQGNIILSTE

101 KSKKLKKRPE ASTTKPKAVD TYCLDYKPSK GRRWAARAPS TRITYGTITK

151 ERDYCTEDQT AESWREEGFP VGLKLAVLGI FIIVVFVYLT VENKPLFG
```

The N-terminal leader sequence consists of amino acid residues 1 to 18 of the insert sequence, and amino acid residues 19 to 198 are the synthetic consensus LEMD1A antigen.

```
Single strand DNA sequence of pGX1431 (SEQ ID NO: 7):
  1 GCTGCTTCGC GATGTACGGG CCAGATATAC GCGTTGACAT TGATTATTGA

51 CTAGTTATTA ATAGTAATCA ATTACGGGGT CATTAGTTCA TAGCCCATAT

101 ATGGAGTTCC GCGTTACATA ACTTACGGTA AATGGCCCGC CTGGCTGACC

151 GCCCAACGAC CCCCGCCCAT TGACGTCAAT AATGACGTAT GTTCCCATAG

201 TAACGCCAAT AGGGACTTTC CATTGACGTC AATGGGTGGA GTATTTACGG

251 TAAACTGCCC ACTTGGCAGT ACATCAAGTG TATCATATGC CAAGTACGCC

301 CCCTATTGAC GTCAATGACG GTAAATGGCC CGCCTGGCAT TATGCCCAGT

351 ACATGACCTT ATGGGACTTT CCTACTTGGC AGTACATCTA CGTATTAGTC

401 ATCGCTATTA CCATGGTGAT GCGGTTTTGG CAGTACATCA ATGGGCGTGG

451 ATAGCGGTTT GACTCACGGG GATTTCCAAG TCTCCACCCC ATTGACGTCA

501 ATGGGAGTTT GTTTTGGCAC CAAAATCAAC GGGACTTTCC AAAATGTCGT

551 AACAACTCCG CCCCATTGAC GCAAATGGGC GGTAGGCGTG TACGGTGGGA

601 GGTCTATATA AGCAGAGCTC TCTGGCTAAC TAGAGAACCC ACTGCTTACT

651 GGCTTATCGA AATTAATACG ACTCACTATA GGGAGACCCA AGCTGGCTAG
```

-continued

```
 701 CGTTTAAACT TAAGCTTGGT ACCGAGCTCG GATCCGCCAC CATGGACTGG
 751 ACCTGGATTC TGTTCCTGGT GGCAGCAGCA ACACGGGTGC ACTCCGTGGA
 801 CGTGAAGTGC CTGTCTGATT GTAAGCTGCA GAACCAGCTG GAGAAGCTGG
 851 CCTTTAGCCC TGGCGCCATC CTGCCATCCA CCAGGAAGCT GGCCGAGAAG
 901 AAGCTGGTGC AGCTGCTGGT GTCCCCACCT TGCGCACCAC CCGTGATGAA
 951 TGGACCCCGC GAGCTGGACG GAGCACAGGA TAGCGACGAT TCCGAGGAGC
1001 TGAACATCAT CCTGCAGGGC AATATCATCC TGTCTACCGA GAAGAGCAAG
1051 AAGCTGAAGA AGCGGCCCGA GGCCTCTACC ACAAAGCCTA AGGCCGTGGA
1101 CACATACTGC CTGGATTATA AGCCATCTAA GGGCCGGAGA TGGGCAGCCA
1151 GGGCCCCAAG CACCCGCATC ACATACGGCA CCATCACAAA GGAGCGGGAC
1201 TATTGTACCG AGGATCAGAC AGCCGAGAGC TGGAGAGAGG AGGGCTTCCC
1251 TGTGGGCCTG AAGCTGGCCG TGCTGGGCAT CTTCATCATC GTGGTGTTCG
1301 TGTACCTGAC AGTGGAGAAC AAGCCACTGT TTGGCTGATA ACTCGAGTCT
1351 AGAGGGCCCG TTTAAACCCG CTGATCAGCC TCGACTGTGC CTTCTAGTTG
1401 CCAGCCATCT GTTGTTTGCC CCTCCCCCGT GCCTTCCTTG ACCCTGGAAG
1451 GTGCCACTCC CACTGTCCTT TCCTAATAAA ATGAGGAAAT TGCATCGCAT
1501 TGTCTGAGTA GGTGTCATTC TATTCTGGGG GGTGGGGTGG GGCAGGACAG
1551 CAAGGGGGAG GATTGGGAAG ACAATAGCAG GCATGCTGGG GATGCGGTGG
1601 GCTCTATGGC TTCTACTGGG CGGTTTTATG GACAGCAAGC GAACCGGAAT
1651 TGCCAGCTGG GGCGCCCTCT GGTAAGGTTG GGAAGCCCTG CAAAGTAAAC
1701 TGGATGGCTT TCTTGCCGCC AAGGATCTGA TGGCGCAGGG GATCAAGCTC
1751 TGATCAAGAG ACAGGATGAG GATCGTTTCG CATGATTGAA CAAGATGGAT
1801 TGCACGCAGG TTCTCCGGCC GCTTGGGTGG AGAGGCTATT CGGCTATGAC
1851 TGGGCACAAC AGACAATCGG CTGCTCTGAT GCCGCCGTGT TCCGGCTGTC
1901 AGCGCAGGGG CGCCCGGTTC TTTTTGTCAA GACCGACCTG TCCGGTGCCC
1951 TGAATGAACT GCAAGACGAG GCAGCGCGGC TATCGTGGCT GGCCACGACG
2001 GGCGTTCCTT GCGCAGCTGT GCTCGACGTT GTCACTGAAG CGGGAAGGGA
2051 CTGGCTGCTA TTGGGCGAAG TGCCGGGGCA GGATCTCCTG TCATCTCACC
2101 TTGCTCCTGC CGAGAAAGTA TCCATCATGG CTGATGCAAT GCGGCGGCTG
2151 CATACGCTTG ATCCGGCTAC CTGCCCATTC GACCACCAAG CGAAACATCG
2201 CATCGAGCGA GCACGTACTC GGATGGAAGC CGGTCTTGTC GATCAGGATG
2251 ATCTGGACGA AGAGCATCAG GGGCTCGCGC CAGCCGAACT GTTCGCCAGG
2301 CTCAAGGCGA GCATGCCCGA CGGCGAGGAT CTCGTCGTGA CCCATGGCGA
2351 TGCCTGCTTG CCGAATATCA TGGTGGAAAA TGGCCGCTTT TCTGGATTCA
2401 TCGACTGTGG CCGGCTGGGT GTGGCGGACC GCTATCAGGA CATAGCGTTG
2451 GCTACCCGTG ATATTGCTGA AGAGCTTGGC GGCGAATGGG CTGACCGCTT
2501 CCTCGTGCTT TACGGTATCG CCGCTCCCGA TTCGCAGCGC ATCGCCTTCT
2551 ATCGCCTTCT TGACGAGTTC TTCTGAATTA TTAACGCTTA CAATTTCCTG
2601 ATGCGGTATT TTCTCCTTAC GCATCTGTGC GGTATTTCAC ACCGCATCAG
2651 GTGGCACTTT TCGGGGAAAT GTGCGCGGAA CCCCTATTTG TTTATTTTTC
```

```
-continued
2701 TAAATACATT CAAATATGTA TCCGCTCATG AGACAATAAC CCTGATAAAT

2751 GCTTCAATAA TAGCACGTGC TAAAACTTCA TTTTTAATTT AAAAGGATCT

2801 AGGTGAAGAT CCTTTTTGAT AATCTCATGA CCAAAATCCC TTAACGTGAG

2851 TTTTCGTTCC ACTGAGCGTC AGACCCCGTA GAAAAGATCA AAGGATCTTC

2901 TTGAGATCCT TTTTTTCTGC GCGTAATCTG CTGCTTGCAA ACAAAAAAAC

2951 CACCGCTACC AGCGGTGGTT TGTTTGCCGG ATCAAGAGCT ACCAACTCTT

3001 TTTCCGAAGG TAACTGGCTT CAGCAGAGCG CAGATACCAA ATACTGTTCT

3051 TCTAGTGTAG CCGTAGTTAG GCCACCACTT CAAGAACTCT GTAGCACCGC

3101 CTACATACCT CGCTCTGCTA ATCCTGTTAC CAGTGGCTGC TGCCAGTGGC

3151 GATAAGTCGT GTCTTACCGG GTTGGACTCA AGACGATAGT TACCGGATAA

3201 GGCGCAGCGG TCGGGCTGAA CGGGGGGTTC GTGCACACAG CCCAGCTTGG

3251 AGCGAACGAC CTACACCGAA CTGAGATACC TACAGCGTGA GCTATGAGAA

3301 AGCGCCACGC TTCCCGAAGG GAGAAAGGCG GACAGGTATC CGGTAAGCGG

3351 CAGGGTCGGA ACAGGAGAGC GCACGAGGGA GCTTCCAGGG GGAAACGCCT

3401 GGTATCTTTA TAGTCCTGTC GGGTTTCGCC ACCTCTGACT TGAGCGTCGA

3451 TTTTTGTGAT GCTCGTCAGG GGGCGGAGC CTATGGAAAA ACGCCAGCAA

3501 CGCGGCCTTT TTACGGTTCC TGGCCTTTTG CTGGCCTTTT GCTCACATGT

3551 TCTT
```

The N-terminal leader sequence consists of nucleotides 1 to 54 of the above sequence, and the remaining nucleotides encode the LEMD1A antigen.

Example 3

Synthetic Consensus LEMD1F

Figures 4A, 4B:
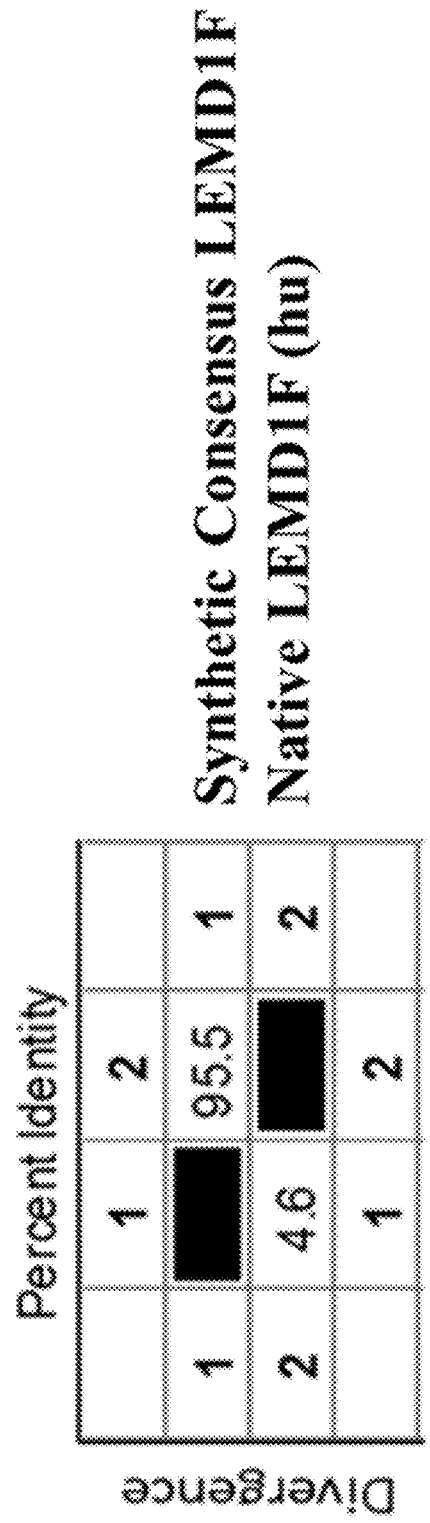
FIG. 4A is a sequence alignment of amino acids 19-84 of synthetic consensus LEMD1F (SEQ ID NO: 14) with native human LEMD1F (SEQ ID NO: 16).
FIG. 4B presents the sequence identity and divergence between native and synthetic consensus LEMD1F.

In order to abolish the potential biological function of the resulting consensus LEMD1F, two mutations in the LEM domain (G20A and P25A) were introduced to disrupt BAF binding. As a result, the synthetic consensus LEMD1F protein shares 95.5% identity with native human LEMD1F protein as shown in FIGS. 4A and 4B.

Once the synthetic consensus LEMD1F DNA sequence was obtained, in order to have a higher level of expression the N-terminal methionine of the synthetic consensus LEMD1F was removed and an upstream Kozak sequence and IgE leader were added to the N-terminus. Furthermore, the codon usage of this gene was adapted to the codon bias of Homo sapiens genes. In addition, RNA optimization was also-performed: regions of very high (>80%) or very low (<30%) GC content and the cis-acting sequence motifs such as internal TATA boxes, chi-sites and ribosomal entry sites were avoided. A schematic of the synthetic consensus protein is presented in FIG. 5. Table 4 presents some characteristics of synthetic consensus LEMD1F.

TABLE 4

Characteristics of LEMD1F

| Characteristics | Synthetic Consensus LEMD1F |
| --- | --- |
| Identity to native human LEMD1F | 95.5% |
| Identity to native rhesus LEMD1F | 55.2-61.2% |

TABLE 4-continued

Characteristics of LEMD1F

| Characteristics | Synthetic Consensus LEMD1F |
| --- | --- |
| Identity to native mouse LEMD1F | 11.9-43.3% |
| Number of amino acid mutations (vs native human) | 3 |
| Number of inserted mutations (not consensus derived) | 2 |
| Molecular weight | 86 aa (9.5 kDa) |
| Length of coding sequence (bp) | 258 |

An expression vector, pGX1432 was constructed using the same pGX0001 backbone as used for the construction of pGX1431. Referring to FIG. 6, the synthesized synthetic consensus LEMD1F was digested with BamHI and XhoI, and cloned into expression vector pGX0001 (Inovio Pharmaceuticals) with the expression cassette placed under the transcriptional control of the cytomegalovirus immediate-early promoter. The resulting plasmid was designated pGX1432 and the full length sequence was confirmed. Features of pGX1432 are provided in Table 5.

TABLE 5

| Elements: | Base Pairs: |
| --- | --- |
| hCMV Promoter: | 137-724 |
| Synthetic Consensus LEMD1F Coding Sequence: | 742-999 |
| bGH PolyA: | 1043-1267 |
| Kanamycin Resistance (KanR): | 1440-2234 |
| pUC Ori: | 2533-3206 |

Amino acid insert sequence of pGX1432 (SEQ ID NO: 4):
```
  1 MDWTWILFLV AAATRVHSVD VKCLSDCKLQ NQLEKLAFSP GAILRGLQEH

51 QAPESHMGLS PKRETTARKT RLLRAGEKKV SQWA
```

The N-terminal leader sequence consists of amino acid residues 1 to 18 of the insert sequence, and amino acid residues 19 to 84 are the synthetic consensus LEMD1F antigen.

```
Single strand DNA sequence of pGX1432 (SEQ ID NO: 8):
    1 GCTGCTTCGC GATGTACGGG CCAGATATAC GCGTTGACAT TGATTATTGA

51 CTAGTTATTA ATAGTAATCA ATTACGGGGT CATTAGTTCA TAGCCCATAT

101 ATGGAGTTCC GCGTTACATA ACTTACGGTA AATGGCCCGC CTGGCTGACC

151 GCCCAACGAC CCCCGCCCAT TGACGTCAAT AATGACGTAT GTTCCCATAG

201 TAACGCCAAT AGGGACTTTC CATTGACGTC AATGGGTGGA GTATTTACGG

251 TAAACTGCCC ACTTGGCAGT ACATCAAGTG TATCATATGC CAAGTACGCC

301 CCCTATTGAC GTCAATGACG GTAAATGGCC CGCCTGGCAT TATGCCCAGT

351 ACATGACCTT ATGGGACTTT CCTACTTGGC AGTACATCTA CGTATTAGTC

401 ATCGCTATTA CCATGGTGAT GCGGTTTTGG CAGTACATCA ATGGGCGTGG

451 ATAGCGGTTT GACTCACGGG GATTTCCAAG TCTCCACCCC ATTGACGTCA

501 ATGGGAGTTT GTTTTGGCAC CAAAATCAAC GGGACTTTCC AAAATGTCGT

551 AACAACTCCG CCCCATTGAC GCAAATGGGC GGTAGGCGTG TACGGTGGGA

601 GGTCTATATA AGCAGAGCTC TCTGGCTAAC TAGAGAACCC ACTGCTTACT

651 GGCTTATCGA AATTAATACG ACTCACTATA GGGAGACCCA AGCTGGCTAG

701 CGTTTAAACT TAAGCTTGGT ACCGAGCTCG GATCCGCCAC CATGGACTGG

751 ACCTGGATTC TGTTCCTGGT GGCAGCAGCA ACAAGGGTGC ACTCTGTGGA

801 CGTGAAGTGC CTGAGCGATT GTAAGCTGCA GAACCAGCTG GAGAAGCTGG

851 CCTTTTCCCC AGGAGCAATC CTGAGGGGAC TGCAGGAGCA CCAGGCACCA

901 GAGAGCCACA TGGGACTGTC CCCTAAGCGG GAGACCACAG CAAGGAAGAC

951 CAGACTGCTG AGGGCAGGAG AGAAGAAGGT GTCTCAGTGG GCCTGATAAC

1001 TCGAGTCTAG AGGGCCCGTT TAAACCCGCT GATCAGCCTC GACTGTGCCT

1051 TCTAGTTGCC AGCCATCTGT TGTTTGCCCC TCCCCCGTGC CTTCCTTGAC

1101 CCTGGAAGGT GCCACTCCCA CTGTCCTTTC CTAATAAAAT GAGGAAATTG

1151 CATCGCATTG TCTGAGTAGG TGTCATTCTA TTCTGGGGGG TGGGGTGGGG

1201 CAGGACAGCA AGGGGGAGGA TTGGGAAGAC AATAGCAGGC ATGCTGGGGA

1251 TGCGGTGGGC TCTATGGCTT CTACTGGGCG GTTTTATGGA CAGCAAGCGA

1301 ACCGGAATTG CCAGCTGGGG CGCCCTCTGG TAAGGTTGGG AAGCCCTGCA

1351 AAGTAAACTG GATGGCTTTC TTGCCGCCAA GGATCTGATG GCGCAGGGGA

1401 TCAAGCTCTG ATCAAGAGAC AGGATGAGGA TCGTTTCGCA TGATTGAACA

1451 AGATGGATTG CACGCAGGTT CTCCGGCCGC TTGGGTGGAG AGGCTATTCG

1501 GCTATGACTG GGCACAACAG ACAATCGGCT GCTCTGATGC CGCCGTGTTC

1551 CGGCTGTCAG CGCAGGGGCG CCCGGTTCTT TTTGTCAAGA CCGACCTGTC

1601 CGGTGCCCTG AATGAACTGC AAGACGAGGC AGCGCGGCTA TCGTGGCTGG

1651 CCACGACGGG CGTTCCTTGC GCAGCTGTGC TCGACGTTGT CACTGAAGCG
```

```
1701 GGAAGGGACT GGCTGCTATT GGGCGAAGTG CCGGGGCAGG ATCTCCTGTC

1751 ATCTCACCTT GCTCCTGCCG AGAAAGTATC CATCATGGCT GATGCAATGC

1801 GGCGGCTGCA TACGCTTGAT CCGGCTACCT GCCCATTCGA CCACCAAGCG

1851 AAACATCGCA TCGAGCGAGC ACGTACTCGG ATGGAAGCCG GTCTTGTCGA

1901 TCAGGATGAT CTGGACGAAG AGCATCAGGG GCTCGCGCCA GCCGAACTGT

1951 TCGCCAGGCT CAAGGCGAGC ATGCCCGACG GCGAGGATCT CGTCGTGACC

2001 CATGGCGATG CCTGCTTGCC GAATATCATG GTGGAAAATG CCGCTTTTC

2051 TGGATTCATC GACTGTGGCC GGCTGGGTGT GGCGGACCGC TATCAGGACA

2101 TAGCGTTGGC TACCCGTGAT ATTGCTGAAG AGCTTGGCGG CGAATGGGCT

2151 GACCGCTTCC TCGTGCTTTA CGGTATCGCC GCTCCCGATT CGCAGCGCAT

2201 CGCCTTCTAT CGCCTTCTTG ACGAGTTCTT CTGAATTATT AACGCTTACA

2251 ATTTCCTGAT GCGGTATTTT CTCCTTACGC ATCTGTGCGG TATTTCACAC

2301 CGCATCAGGT GGCACTTTTC GGGGAAATGT GCGCGGAACC CCTATTTGTT

2351 TATTTTTCTA AATACATTCA AATATGTATC CGCTCATGAG ACAATAACCC

2401 TGATAAATGC TTCAATAATA GCACGTGCTA AAACTTCATT TTTAATTTAA

2451 AAGGATCTAG GTGAAGATCC TTTTTGATAA TCTCATGACC AAAATCCCTT

2501 AACGTGAGTT TTCGTTCCAC TGAGCGTCAG ACCCCGTAGA AAAGATCAAA

2551 GGATCTTCTT GAGATCCTTT TTTTCTGCGC GTAATCTGCT GCTTGCAAAC

2601 AAAAAAACCA CCGCTACCAG CGGTGGTTTG TTTGCCGGAT CAAGAGCTAC

2651 CAACTCTTTT TCCGAAGGTA ACTGGCTTCA GCAGAGCGCA GATACCAAAT

2701 ACTGTTCTTC TAGTGTAGCC GTAGTTAGGC CACCACTTCA AGAACTCTGT

2751 AGCACCGCCT ACATACCTCG CTCTGCTAAT CCTGTTACCA GTGGCTGCTG

2801 CCAGTGGCGA TAAGTCGTGT CTTACCGGGT TGGACTCAAG ACGATAGTTA

2851 CCGGATAAGG CGCAGCGGTC GGGCTGAACG GGGGGTTCGT GCACACAGCC

2901 CAGCTTGGAG CGAACGACCT ACACCGAACT GAGATACCTA CAGCGTGAGC

2951 TATGAGAAAG CGCCACGCTT CCCGAAGGGA GAAAGGCGGA CAGGTATCCG

3001 GTAAGCGGCA GGGTCGGAAC AGGAGAGCGC ACGAGGGAGC TTCCAGGGGG

3051 AAACGCCTGG TATCTTTATA GTCCTGTCGG GTTTCGCCAC CTCTGACTTG

3101 AGCGTCGATT TTTGTGATGC TCGTCAGGGG GGCGGAGCCT ATGGAAAAAC

3151 GCCAGCAACG CGGCCTTTTT ACGGTTCCTG GCCTTTTGCT GGCCTTTTGC

3201 TCACATGTTC TT
```

The N-terminal leader sequence consists of nucleotides 1 to 54 of the above sequence, and the remaining nucleotides encode the LEMD1F antigen.

Example 3

Synthetic Consensus LEMD1AF

Figure 7:
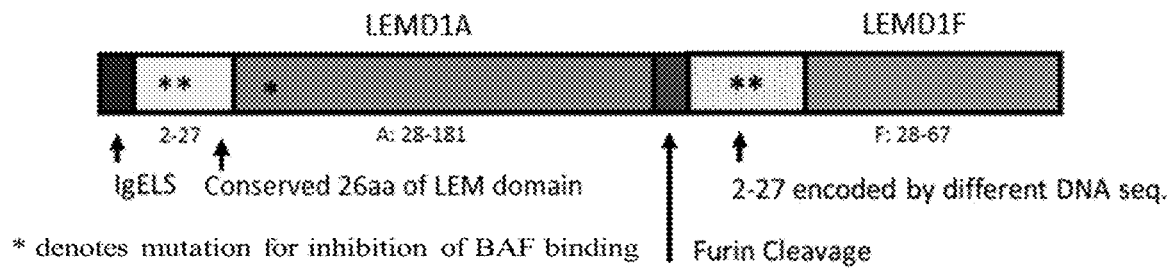
FIG. 7 is a schematic representation of synthetic consensus LEMD1AF.

A multi-antigen construct, synthetic consensus LEMD1AF was created by inserting a furin cleavage site (RGRKRRS, SEQ ID NO: 10) between the amino acid sequences of synthetic consensus LEMD1A and synthetic consensus LEMD1F. Once the synthetic consensus LEMD1AF DNA sequence was obtained, in order to have a higher level of expression the N-terminal methionine of the synthetic consensus LEMD1AF was removed and an upstream Kozak sequence and IgE leader were added to the N-terminus. Furthermore, the codon usage of this gene was adapted to the codon bias of *Homo sapiens* genes. In addition, RNA optimization was also performed: regions of very high (>80%) or very low (<30%) GC content and the cis-acting sequence motifs such as internal TATA boxes, chi-sites and ribosomal entry sites were avoided. As the N-terminal domains (amino acids 2-27) in both consensus LEMD1A and consensus LEMD1F proteins are identical, the DNA sequences encoding the amino acid 2-27 region of synthetic consensus LEMD1A and and the amino acid 2-27 region of synthetic consensus LEMD1F were optimized differently (64.1% sequence identity) to increase the plasmid stability. A schematic representation of the synthetic consensus LEMD1AF construct is shown in FIG. 7.

Figure 8:
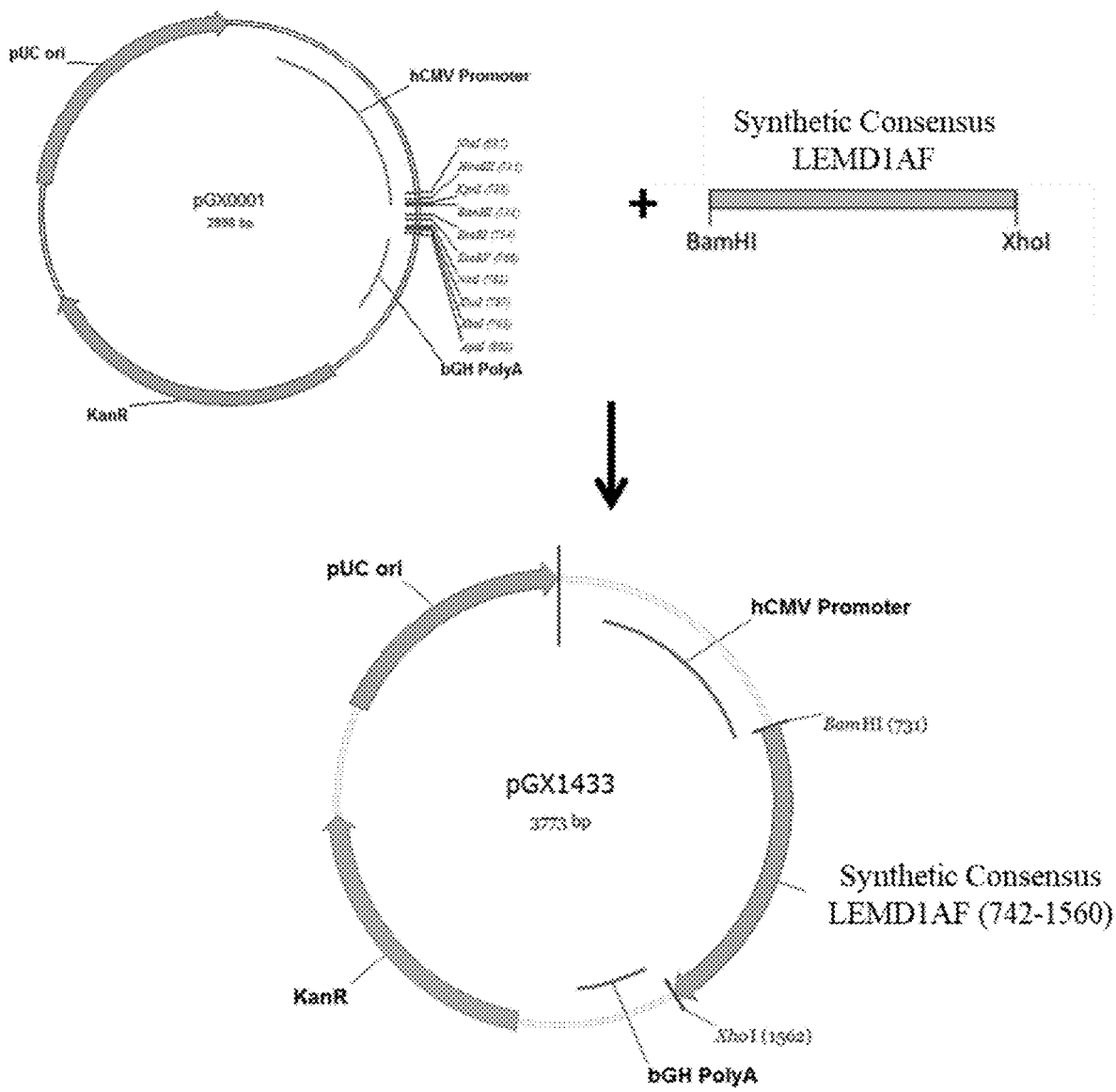
FIG. 8 illustrates the cloning strategy employed to generate pGX1433.
Figure 9:
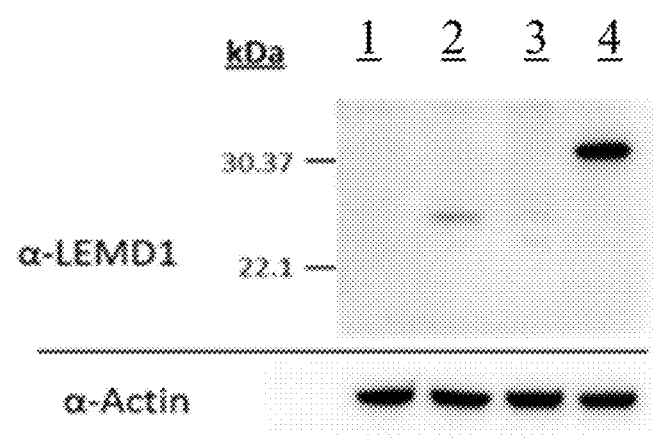
FIG. 9 shows a Western blot to determine expression of synthetic consensus LEMD1A, LEMD1F, and LEMD1AF generated from constructs pGX1431, pGX1432, and pGX1433, respectively, in rhabdomyosarcoma cells.

Referring to FIG. 8, the synthesized synthetic consensus LEMD1AF was digested with BamHI and XhoI, and cloned into expression vector pGX0001 (Inovio Pharmaceuticals) as described in previous examples. The expression cassette was placed under the transcriptional control of the cytomegalovirus immediate-early promoter. The resulting plasmid was designated pGX1433 and the full length sequence was confirmed.

pGX1433 is a DNA plasmid encoding the synthetic consensus LEMD1AF protein. Related mRNA production is driven by a human CMV promoter (hCMV promoter) and terminated by the bovine growth hormone 3' end polyadenylation signal (bGH polyA). The pGX0001 backbone includes the kanamycin resistance gene (KanR) and plasmid origin of replication (pUC ori) for production purpose. Those elements are not functional in eukaryotic cells. Table 6 provides additional information related to pGX1433.

TABLE 6

| Elements: | Base Pairs: |
|---|---|
| hCMV Promoter: | 137-724 |
| Synthetic Consensus LEMD1AF Coding Sequence: | 742-1560 |
| bGH PolyA | 1604-1828 |
| Kanamycin Resistance (KanR): | 2001-2795 |
| pUC Ori | 3094-3767 |

```
Amino acid insert sequence of pGX1433
                                                          (SEQ ID NO: 6)
    1 MDWTWILFLV AAATRVHSVD VKCLSDCKLQ NQLEKLAFSP GAILPSTRKL

51 AEKKLVQLLV SPPCAPPVMN GPRELDGAQD SDDSEELNII LQGNIILSTE

101 KSKKLKKRPE ASTTKPKAVD TYCLDYKPSK GRRWAARAPS TRITYGTITK

151 ERDYCTEDQT AESWREEGFP VGLKLAVLGI FIIVVFVYLT VENKPLFGRG

201 RKRRSVDVKC LSDCKLQNQL EKLAFSPGAI LRGLQEHQAP ESHMGLSPKR

251 ETTARKTRLL RAGEKKVSQW A
```

The N-terminal leader sequence consists of amino acid residues 1 to 18 of the insert sequence, and amino acid residues 19 to 198 and 206-271 are the synthetic consensus LEMD1A and F antigens. A furin cleavage site, amino acid residues 199 to 205, resides between the LEMD1 sequences.

```
Single strand DNA sequence of pGX1433 (SEQ ID NO: 9):
    1 GCTGCTTCGC GATGTACGGG CCAGATATAC GCGTTGACAT TGATTATTGA

51 CTAGTTATTA ATAGTAATCA ATTACGGGGT CATTAGTTCA TAGCCCATAT

101 ATGGAGTTCC GCGTTACATA ACTTACGGTA AATGGCCCGC CTGGCTGACC

151 GCCCAACGAC CCCCGCCCAT TGACGTCAAT AATGACGTAT GTTCCCATAG

201 TAACGCCAAT AGGGACTTTC CATTGACGTC AATGGGTGGA GTATTTACGG

251 TAAACTGCCC ACTTGGCAGT ACATCAAGTG TATCATATGC CAAGTACGCC

301 CCCTATTGAC GTCAATGACG GTAAATGGCC CGCCTGGCAT TATGCCCAGT

351 ACATGACCTT ATGGGACTTT CCTACTTGGC AGTACATCTA CGTATTAGTC

401 ATCGCTATTA CCATGGTGAT GCGGTTTTGG CAGTACATCA ATGGGCGTGG

451 ATAGCGGTTT GACTCACGGG GATTTCCAAG TCTCCACCCC ATTGACGTCA

501 ATGGGAGTTT GTTTTGGCAC CAAAATCAAC GGGACTTTCC AAAATGTCGT

551 AACAACTCCG CCCCATTGAC GCAAATGGGC GGTAGGCGTG TACGGTGGGA

601 GGTCTATATA AGCAGAGCTC TCTGGCTAAC TAGAGAACCC ACTGCTTACT

651 GGCTTATCGA AATTAATACG ACTCACTATA GGGAGACCCA AGCTGGCTAG

701 CGTTTAAACT TAAGCTTGGT ACCGAGCTCG GATCCGCCAC CATGGACTGG

751 ACCTGGATTC TGTTCCTGGT GGCAGCAGCA ACCCGCGTGC ATTCCGTCGA

801 TGTGAAGTGT CTGAGTGATT GTAAACTGCA GAACCAGCTG GAGAAGCTGG

851 CCTTTAGCCC TGGAGCAATC CTGCCATCCA CCAGGAAGCT GGCCGAGAAG

901 AAGCTGGTGC AGCTGCTGGT GAGCCCACCT TGCGCACCAC CGTGATGAA
```

-continued

```
 951 TGGCCCAAGA GAGCTGGACG GCGCCCAGGA TAGCGACGAT TCCGAGGAGC

1001 TGAACATCAT CCTGCAGGGC AATATCATCC TGTCTACCGA GAAGAGCAAG

1051 AAGCTGAAGA AGCGGCCCGA GGCCTCCACC ACAAAGCCTA AGGCCGTGGA

1101 CACATACTGC CTGGATTATA AGCCTTCCAA GGGCCGGAGA TGGGCAGCCA

1151 GGGCCCCATC TACCAGGATC ACATACGGCA CCATCACAAA GGAGCGGGAC

1201 TATTGTACCG AGGATCAGAC AGCCGAGTCT TGGAGAGAGG AGGGATTCCC

1251 AGTGGGCCTG AAGCTGGCCG TGCTGGGCAT CTTCATCATC GTGGTGTTCG

1301 TGTACCTGAC AGTGGAGAAC AAGCCTCTGT TTGGCCGGGG CAGAAAGAGG

1351 CGCTCTGTGG ATGTAAAATG CCTATCGGAC TGCAAGTTGC AAAATCAATT

1401 AGAAAAATTG GCCTTCTCCC CAGGGGCGAT ATTGAGGGGC CTGCAGGAGC

1451 ACCAGGCACC AGAGTCCCAC ATGGGCCTGT CTCCCAAGCG CGAGACAACC

1501 GCAAGAAAAA CAAGGCTGCT GAGGGCTGGG GAAAAGAAAG TGTCACAGTG

1551 GGCATGATAA CTCGAGTCTA GAGGGCCCGT TTAAACCCGC TGATCAGCCT

1601 CGACTGTGCC TTCTAGTTGC CAGCCATCTG TTGTTTGCCC CTCCCCCGTG

1651 CCTTCCTTGA CCCTGGAAGG TGCCACTCCC ACTGTCCTTT CCTAATAAAA

1701 TGAGGAAATT GCATCGCATT GTCTGAGTAG GTGTCATTCT ATTCTGGGGG

1751 GTGGGGTGGG GCAGGACAGC AAGGGGGAGG ATTGGGAAGA CAATAGCAGG

1801 CATGCTGGGG ATGCGGTGGG CTCTATGGCT TCTACTGGGC GGTTTTATGG

1851 ACAGCAAGCG AACCGGAATT GCCAGCTGGG GCGCCCTCTG GTAAGGTTGG

1901 GAAGCCCTGC AAAGTAAACT GGATGGCTTT CTTGCCGCCA AGGATCTGAT

1951 GGCGCAGGGG ATCAAGCTCT GATCAAGAGA CAGGATGAGG ATCGTTTCGC

2001 ATGATTGAAC AAGATGGATT GCACGCAGGT TCTCCGGCCG CTTGGGTGGA

2051 GAGGCTATTC GGCTATGACT GGGCACAACA GACAATCGGC TGCTCTGATG

2101 CCGCCGTGTT CCGGCTGTCA GCGCAGGGGC GCCCGGTTCT TTTTGTCAAG

2151 ACCGACCTGT CCGGTGCCCT GAATGAACTG CAAGACGAGG CAGCGCGGCT

2201 ATCGTGGCTG GCCACGACGG GCGTTCCTTG CGCAGCTGTG CTCGACGTTG

2251 TCACTGAAGC GGGAAGGGAC TGGCTGCTAT TGGGCGAAGT GCCGGGGCAG

2301 GATCTCCTGT CATCTCACCT TGCTCCTGCC GAGAAAGTAT CCATCATGGC

2351 TGATGCAATG CGGCGGCTGC ATACGCTTGA TCCGGCTACC TGCCCATTCG

2401 ACCACCAAGC GAAACATCGC ATCGAGCGAG CACGTACTCG GATGGAAGCC

2451 GGTCTTGTCG ATCAGGATGA TCTGGACGAA GAGCATCAGG GGCTCGCGCC

2501 AGCCGAACTG TTCGCCAGGC TCAAGGCGAG CATGCCCGAC GGCGAGGATC

2551 TCGTCGTGAC CCATGGCGAT GCCTGCTTGC CGAATATCAT GGTGGAAAAT

2601 GGCCGCTTTT CTGGATTCAT CGACTGTGGC CGGCTGGGTG TGGCGGACCG

2651 CTATCAGGAC ATAGCGTTGG CTACCCGTGA TATTGCTGAA GAGCTTGGCG

2701 GCGAATGGGC TGACCGCTTC CTCGTGCTTT ACGGTATCGC CGCTCCCGAT

2751 TCGCAGCGCA TCGCCTTCTA TCGCCTTCTT GACGAGTTCT TCTGAATTAT

2801 TAACGCTTAC AATTTCCTGA TGCGGTATTT TCTCCTTACG CATCTGTGCG

2851 GTATTTCACA CCGCATCAGG TGGCACTTTT CGGGGAAATG TGCGCGGAAC

2901 CCCTATTTGT TTATTTTTCT AAATACATTC AAATATGTAT CCGCTCATGA
```

```
-continued
2951 GACAATAACC CTGATAAATG CTTCAATAAT AGCACGTGCT AAAACTTCAT

3001 TTTTAATTTA AAAGGATCTA GGTGAAGATC CTTTTTGATA ATCTCATGAC

3051 CAAAATCCCT TAACGTGAGT TTTCGTTCCA CTGAGCGTCA GACCCCGTAG

3101 AAAAGATCAA AGGATCTTCT TGAGATCCTT TTTTTCTGCG CGTAATCTGC

3151 TGCTTGCAAA CAAAAAAACC ACCGCTACCA GCGGTGGTTT GTTTGCCGGA

3201 TCAAGAGCTA CCAACTCTTT TTCCGAAGGT AACTGGCTTC AGCAGAGCGC

3251 AGATACCAAA TACTGTTCTT CTAGTGTAGC CGTAGTTAGG CCACCACTTC

3301 AAGAACTCTG TAGCACCGCC TACATACCTC GCTCTGCTAA TCCTGTTACC

3351 AGTGGCTGCT GCCAGTGGCG ATAAGTCGTG TCTTACCGGG TTGGACTCAA

3401 GACGATAGTT ACCGGATAAG GCGCAGCGGT CGGGCTGAAC GGGGGGTTCG

3451 TGCACACAGC CCAGCTTGGA GCGAACGACC TACACCGAAC TGAGATACCT

3501 ACAGCGTGAG CTATGAGAAA GCGCCACGCT TCCCGAAGGG AGAAAGGCGG

3551 ACAGGTATCC GGTAAGCGGC AGGGTCGGAA CAGGAGAGCG CACGAGGGAG

3601 CTTCCAGGGG GAAACGCCTG GTATCTTTAT AGTCCTGTCG GGTTTCGCCA

3651 CCTCTGACTT GAGCGTCGAT TTTTGTGATG CTCGTCAGGG GGGCGGAGCC

3701 TATGGAAAAA CGCCAGCAAC GCGGCCTTTT TACGGTTCCT GGCCTTTTGC

3751 TGGCCTTTTG CTCACATGTT CTT
```

The N-terminal leader sequence consists of nucleotides 1 to 54 of the above sequence, and nucleotides 55 to 594 and 616 to 819 encode the LEMD1AF antigen construct. Nucleotides 595 to 615 encode the furin binding site.

Example 4

In Vitro Antigen Expression

Expression of the antigen protein by pGX1431, pGX1432, and pGX1433 was confirmed by Western blotting. Human rhabdomyosarcoma (RD) cells (ATCC, CCL-136) maintained in DMEM medium with 10% FBS (ThermoFisher) were transfected with pGX1431, pGX1432, pGX1433 or pGX0001 (6 μg/10 $cm^2$ dish) using Turbofectin 8 (Origene). Forty-eight hours after transfection, the cells were lysed using RIPA cell lysis buffer (ThermoFisher) and cell lysate was collected. Following a BCA assay (ThermoFisher) to determine total protein concentration, 15 μg of cell lysate was electrophoresed on a 4-12% SDS-PAGE gel and detection was performed with an anti-LEMD1 monoclonal antibody (Abcam, clone ab201206) then visualized with horseradish peroxidase (HRP)-conjugated anti-rabbit IgG (Santa Cruz Biotech, SC-2004) using an ECL western blot analysis system (GE Amersham). As a loading control, blots were re-probed for actin expression using an anti-β-actin monoclonal antibody (Santa Cruz Biotech, clone, C4).

Protein bands of the expected molecular weights for the synthetic consensus LEMD1A (pGX1431) and synthetic consensus LEMD1AF (pGX1433) constructs were detected, but a band was not detected for the synthetic consensus LEMD1F (pGX1432) construct (FIG. 9). It can be inferred that that LEMD1F antigen was expressed as part of the LEMD1AF antigen because it was detected at the expected molecular weight for the AF antigen. No protein bands were detected in the pGX0001 lane. Anti-β-actin bands were detected of similar intensities indicating equal amounts of protein were loaded in each lane. In summary, pGX1431 and pGX1433 were found to express their respective antigen proteins.

Example 5

Immunogenicity of the Synthetic Consensus LEMD1 Vaccine Constructs

Materials and Methods

Animals and Immunizations

Female, 8-week-old CB6F1 mice were purchased from Jackson Laboratories. All animals were housed in a temperature-controlled, light-cycled facility at BTS Research (San Diego, Calif.). Animal care was carried out according to the guidelines of the National Institutes of Health and the Animal Care and Use Proposal (ACUP) (BTS ACUP #15-091). Mice were divided into ten groups as detailed in Table 1.

TABLE 7

| Group | n | Construct | Construct Dose (μg) | Injection volume (μL) |
|---|---|---|---|---|
| 1 | 4 | pGX0001 | 30 | 30 |
| 2 | 8 | pGX1431 | 10 | 30 |
| 3 | 8 | pGX1431 | 30 | 30 |
| 4 | 8 | pGX1431 | 50 | 30 |
| 5 | 8 | pGX1432 | 10 | 30 |
| 6 | 8 | pGX1432 | 30 | 30 |
| 7 | 8 | pGX1432 | 50 | 30 |
| 8 | 8 | pGX1433 | 10 | 30 |
| 9 | 8 | pGX1433 | 30 | 30 |
| 10 | 8 | pGX1433 | 50 | 30 |

The mice in the immunized groups were vaccinated with the doses indicated of pGX0001, pGX1431, pGX1432, or pGX1433. Briefly, plasmids were formulated in sterile water for injection (VetOne) such that the indicated dose was delivered by intramuscular injection into the tibialis anterior muscle in a 30 µL injection volume. Each intramuscular injection was immediately followed by electroporation (EP) using the CELLECTRA® 2000 Adaptive Constant Current Electroporation Device with a 3P array (Inovio Pharmaceuticals). The device was configured to deliver two 0.1 Amp pulses of 52 ms pulse width, spaced apart by a 1 second delay. The mice received 3 immunizations, 3 weeks apart. Mice were sacrificed one week after the last immunization and spleens harvested for cellular immune readouts. No other tissue was collected.

Splenic Lymphocyte Isolation

Splenocytes were aseptically isolated and placed in 5 mL of R10 media (Rosewell Park Memorial Institute medium 1640 supplemented with 10% fetal bovine serum and 1% antibiotic-antimycotic). Splenocytes were isolated by mechanical disruption of the spleen using a Stomacher machine (Seward Laboratory Systems Inc.), and the resulting product was filtered using a 40-µm cell strainer (BD Falcon). The resulting product was centrifuged and the pellet was treated for 5 min with ACK lysis buffer (Lonza) for lysis of RBCs. The splenocytes were then centrifuged, washed in PBS, and then resuspended in R10 media and immediately used for further analysis.

IFNγ ELISpot

Mouse IFNγ ELISpot assay (MabTech) was performed to evaluate antigen-specific cellular responses. Briefly, 96 well plates pre-coated with anti-mouse IFNγ antibody were washed in PBS and blocked for 2 hours at room temperature with complete culture medium media (RPMI 1640 supplemented with 10% FBS and antibiotics). Splenic lymphocytes were re-suspended in R10 media (and then added in triplicates at an input cell number of $2 \times 10^5$ cells per well. A set of peptides was synthesized (GenScript), each containing 15 amino acid residues overlapping by 9 amino acids representing the entire synthetic consensus LEMD1 protein sequence. These sets of peptides were resuspended in DMSO (Sigma) and pooled at a concentration of ~2 µg/ml peptide into two peptide pools. One peptide pool contained the peptides corresponding to the synthetic consensus LEMD1A antigen protein and the second peptide pool contained the peptides corresponding the synthetic consensus LEMD1F antigen protein. Concavalin A (Sigma) at 5 µg/ml was used as a positive control and complete culture medium was used as a negative control. Plates were incubated for 18 hours at 37° C., in a 5% CO2 atmosphere incubator. Then, a biotinylated anti-mouse IFNγ detection antibody (MabTech) was added, and plates were incubated for 2 hours at room temperature. The plates were washed, and Streptavidin-ALP antibody (MabTech) was added and plates incubated for 1 hour at room temperature. Spot detection was completed according to the kit manufacturer's instructions (MabTech). The spots on the plates were counted using an automated ELISPOT reader (Cellular Technology). The average number of Spot Forming Units (SFU) was adjusted to $1 \times 10^6$ splenocytes for data display.

Antigen specific responses by IFNγ ELISpot are reported as the number of IFNγ spot forming unit (SFU) per $1 \times 10^6$ splenocytes greater than the SFU in the media only control.

Flow Cytometry

Figure 10:
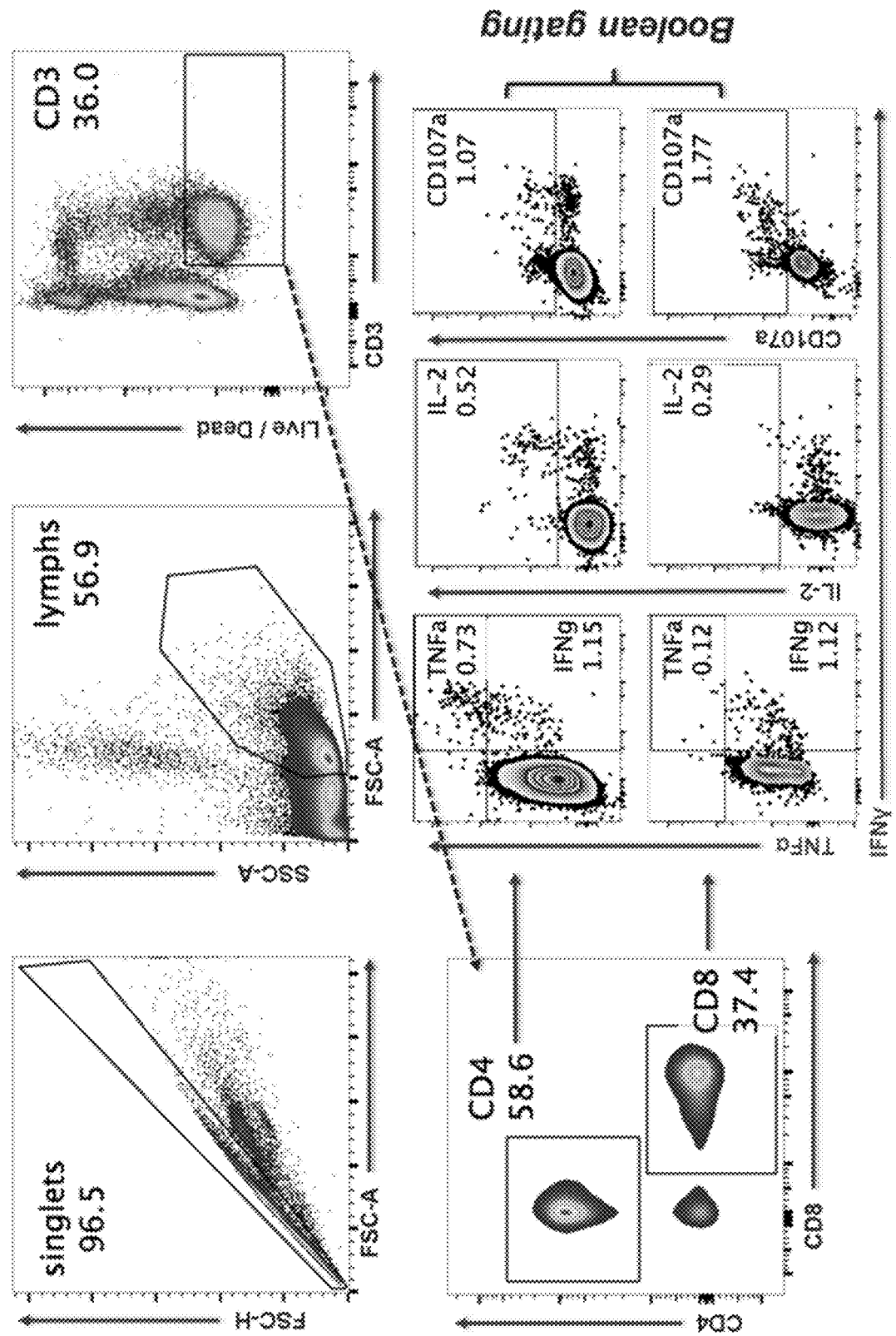
FIG. 10 depicts the flow cytometry gating strategy used characterize cellular immune responses.

Cellular immune responses induced by synthetic consensus LEMD1 were further characterized by flow cytometry. Briefly, $2 \times 10^6$ splenocytes from vaccinated and naïve mice were immediately stimulated following isolation with the synthetic consensus LEMD1 peptide, as appropriate for each group, for 6 hours in the presence of Brefeldin A (BD Biosciences), Monensin (BD Biosciences), and FITC anti-mouse CD107a antibody (BD Biosciences). After stimulation with peptides, splenocytes were spun down and resuspended in 20 µL per well of mouse BD Fc Block (BD Biosciences) solution. The Fc Block is used as an initial dilution of 1:40 in PBS and incubated at 4° C. for 5 minutes. After incubation, the remaining extracellular antibodies (in PBS) are added at 30 µL per well and allowed to incubate at 4° C. for 30 minutes. Upon addition of the extracellular stain, the final volume in each well is 50 µL, consisting of Fc Block at a final dilution of 1:100 and the extracellular antibodies at their appropriate working dilutions. Cells were then stained with viability dye (Vivid V450, Thermo-Fisher) and the following extracellular antibodies: PerCP-Cy5.5 anti-mouse CD4 (BD Biosciences, clone RM4-5) and APC anti-mouse CD8a (BD Biosciences, clone 63-6.7). Cells were fixed and permeabilized (BD Biosciences, #554714) for 20 minutes at 4° C. Intracellular staining was subsequently completed with the following antibodies: APC-Cy7 anti-mouse CD3e (BD Biosciences, clone 145-2C11), BV605 anti-mouse IFNγ (BD Biosciences, clone XMG1.2), APC-R700 anti-mouse IL-2 (BD Biosciences, clone JEs6-5H4), and PE anti-mouse TNF-α (BD Biosciences, clone MP6-XT22). ICS data was collected on 10-color FACS CANTO (BD Biosciences) and analysis completed using FlowJo software. The flow cytometry gating strategy is shown below in FIG. 10.

For a cell to be called antigen specific by flow cytometry, the frequency of the reported parameter must exceed that of the media-only control. For a cell to be identified as producing antigen specific CD107a, the cell must also be identified as positive for antigen specific production of IFNγ, and/or IL-2 and/or TNFα as identified by Boolean gating.

Statistical Analysis

Statistical analysis was completed using IBM SPSS Statistics 22 (IBM Corporation). Analysis between groups was performed using an ANOVA with post-hoc Tukey's Honest Significant Difference (HSD) to adjust for multiple comparisons. Homogeneity of variance was confirmed using the F statistic prior to multiple comparisons. For all statistical analysis, a p-value of 0.050 was considered significant.

Results

IFNγ ELISpot

Immunogenicity of the three synthetic consensus LEMD1 constructs was evaluated at three doses (10 µg, 30 µg, and 50 µg) by IFNγ ELISpot and flow cytometry (n=8/group). Mice were immunized with the empty plasmid backbone (pGX0001) as a negative control (n=4/group). Vaccination with synthetic consensus LEMD1A resulted in significant IFNγ responses compared to negative control vaccinated mice. There was evidence for a dose dependent increase in IFNγ production induced by synthetic consensus LEMD1A (FIG. 11A) with the maximal average response achieved at the 30 µg dose amount. Specifically, synthetic consensus LEMD1A IFNγ SFU were 646±373, 1,683±1248, and 1,645±1002 at 10 µg, 30 µg, and 50 µg, respectively. Synthetic consensus LEMD1A IFNγ responses were significantly greater than naïve (3±4) at the 30 µg (p=0.024) and 50 µg (p=0.028) dose amounts of pGX1431, but not at the 10 µg dose amount (p=0.642). Vaccination with synthetic consensus LEMD1F resulted in minimal IFNγ responses with no evidence for a dose-dependent increase with increasing dose amount (FIG. 11B). LEMD1F IFNγ SFU were 163±382, 88±109, and 140±246 at 10 µg, 30 µg, and 50 µg, respectively. Synthetic consensus LEMD1F IFNγ responses were not significantly greater than naïve (3±4) at the any of the dose amounts of pGX1432. Vaccination with synthetic consensus LEMD1AF resulted in significant IFNγ responses compared to negative control vaccinated mice. There was evidence for a dose dependent increase in IFNγ production induced by synthetic consensus LEMD1AF (FIG. 11C) with the maximal average response achieved at the 50 μg dose amount. Specifically, synthetic consensus LEMD1AF IFNγ SFU were 478±269, 779±392, and 879±552 at 10 μg, 30 μg, and 50 μg, respectively. Synthetic consensus LEMD1AF IFNγ responses were significantly greater than naïve (3±4) at the 30 μg (p=0.018) and 50 μg (p=0.007) dose amounts of pGX1433, but not at the 10 μg dose amount (p=0.227). IFNγ responses are summarized in Table 8.

TABLE 8

IFNγ responses induced by pGX1431, pGX1432, and pGX1433

| Construct | Dose | Mean SFU ± Std. Dev. | p-value |
|---|---|---|---|
| Synthetic Consensus LEMD1A (pGX1431) | | | |
| pGX0001 | 30 μg | 3 ± 4 | n/a |
| pGX1431 | 10 μg | 646 ± 373 | 0.642 |
|  | 30 μg | 1,683 ± 1248 | 0.024 |
|  | 50 μg | 1,645 ± 1002 | 0.028 |
| Synthetic Consensus LEMD1F (pGX1432) | | | |
| pGX0001 | 30 μg | 3 ± 4 | n/a |
| pGX1432 | 10 μg | 163 ± 382 | n/a |
|  | 30 μg | 88 ± 109 | n/a |
|  | 50 μg | 140 ± 246 | n/a |
| Synthetic Consensus LEMD1AF (pGX1433) | | | |
| pGX0001 | 30 μg | 3 ± 4 | n/a |
| pGX1433 | 10 μg | 478 ± 269 | 0.227 |
|  | 30 μg | 779 ± 392 | 0.018 |
|  | 50 μg | 879 ± 552 | 0.007 | p-values reported are relative to naïve (pGX0001 immunized mice).
Significance in assumed at p ≤ 0.05.

Figure 12E:
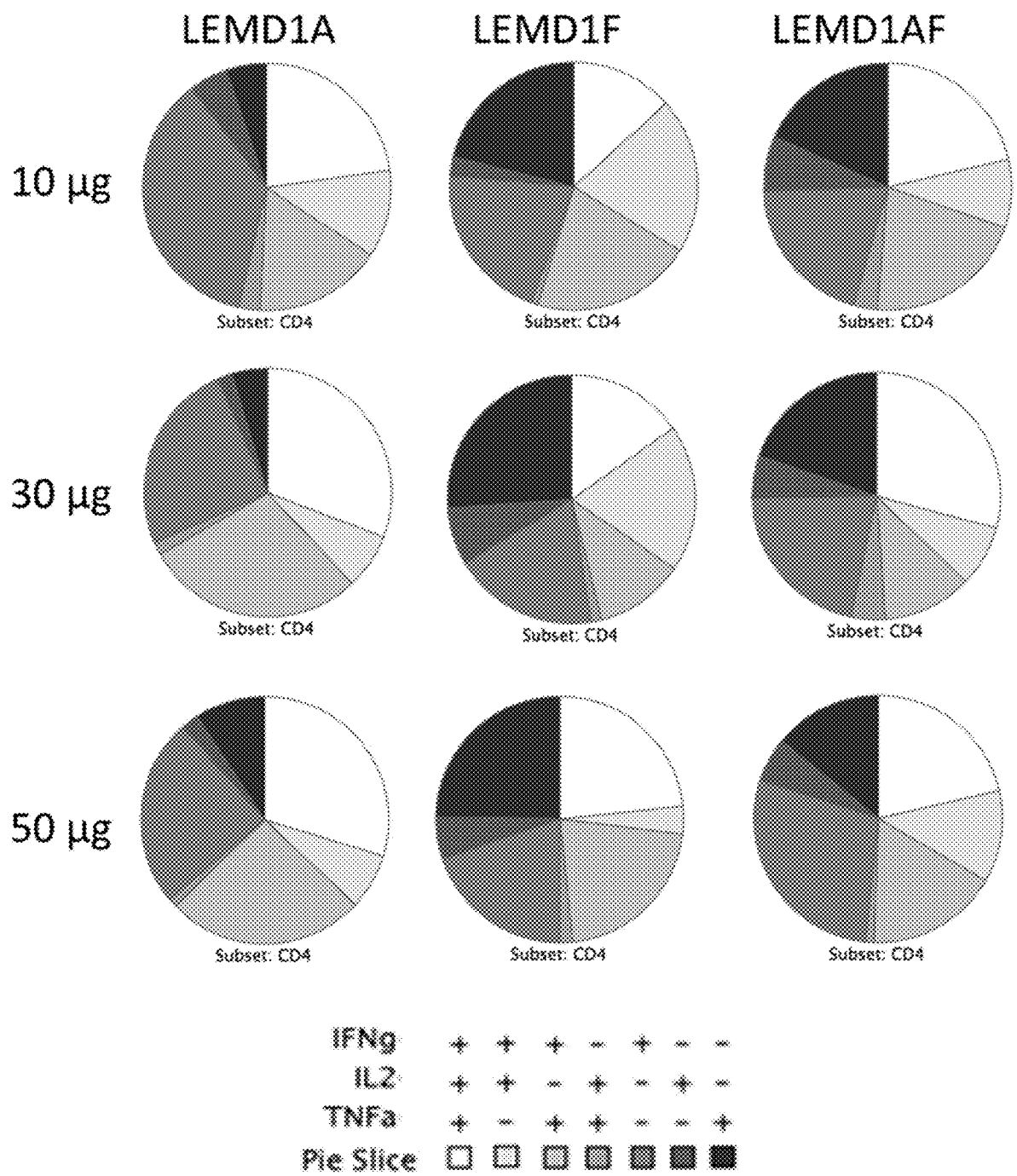
FIG. 12E illustrates the cytokine profile induced by synthetic consensus LEMD1A, LEMD1F, and LEMD1AF in the CD4+ T-cell compartment.

Synthetic consensus LEMD1A induced frequencies of antigen specific CD4+ T cell responses that were significantly more robust than naïve (0.04%±0.03%) at the 50 μg dose amount (1.34%±0.58%) (p<0.005) but not at the 10 μg (0.50%±0.170%) (p<0.004) or 30 μg (1.02%±0.57%) (p<0.122) dose amount groups (FIG. 12A). Synthetic consensus LEMD1A specific CD4+ T cell responses were dose-dependent and consisted mainly of IFNγ+IL-2+ TNFα+IFNγ+IL-2-TNFα+, or IFNγ+IL-2-TNFα− producing CD4+ T cells (FIG. 12E).

Synthetic consensus LEMD1F induced frequencies of antigen specific CD4+ T cell responses that were minimally greater than naïve (0.06%±0.02%). Specifically, pGX1432 induced non-significant responses at the 10 μg dose amount (0.27%±0.34%), 30 μg (0.24%±0.10%) and 50 μg (0.20%±0.20%) dose amount groups (FIG. 12B). Synthetic consensus LEMD1F specific CD4+ T cell responses were dose-dependent and consisted mainly of IFNγ+IL-2+ TNFα+, IFNγ+IL-2+ TNFα−, IFNγ+IL-2-TNFα+, IFNγ-IL-2-TNFα+ or IFNγ+IL-2-TNFα− producing CD4+ T cells (FIG. 12E).

Synthetic consensus LEMD1AF induced frequencies of antigen specific CD4+ T cell responses that were significantly more robust than naïve (0.09%±0.03%) at the 50 μg dose amount (0.80%±0.51%) (p<0.006) but not at the 10 μg (0.53%±0.19%) (p<0.135) or 30 μg (0.50%±0.20%) (p<0.176) dose amount groups (FIG. 12C). Synthetic consensus LEMD1AF specific CD4+ T cell responses were dose-independent and consisted mainly of IFNγ+IL-2+ TNFα+IFNγ+IL-2-TNFα+, IFNγ+IL-2-TNFα- or IFNγ-IL-2-TNFα+ producing CD4+ T cells (FIG. 12E).

The frequency of antigen specific CD4+ T cells is further detailed in Table 9.

All dose amounts of synthetic consensus LEMD1 constructs induced a frequency of CD4+CD107a+ T cells that was slightly greater than naïve but only the pGX1431 construct at the highest dose amount was significantly more robust.

Figure 13A:
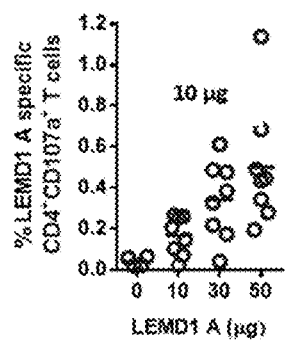
FIG. 13A, FIG. 13B, and FIG. 13C graphically illustrate the cytolytic potential of antigen specific CD4+CD107a+ T-cells induced by synthetic consensus LEMD1A, synthetic consensus LEMD1F, and synthetic consensus LEMD1AF, respectively.

Specifically, the frequency of pGX1431 antigen specific CD4+CD107a+ T cells was 0.17%±0.09%, 0.34%±0.19%, and 0.50%±0.30% in the 10 μg (p=0.532), 30 μg (p=0.314), and 50 μg (p=0.002) dose amounts groups, respectively (FIG. 13A). The cytokine profile of pGX1431 specific CD4+CD107a+ T cells was similar across dose amount groups and was comprised mainly of IFNγ+IL-2+ TNFα+, IFNγ+IL-2-TNFα+, and IFNγ+IL-2-TNFα− cells (FIG. 13E).

Figure 13B:
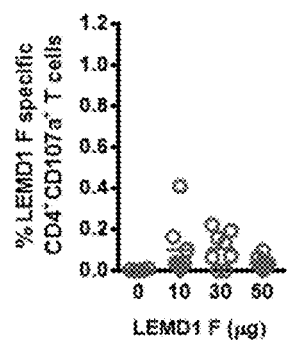

The frequency of pGX1432 antigen specific CD4+ CD107a+ T cells was 0.10%±0.14%, 0.11%±0.08%, and 0.04%±0.03% in the 10 μg, 30 μg, and 50 μg dose amount groups, respectively (FIG. 13B). The cytokine profile of pGX1432 specific CD4+CD107a+ T cells was similar at the 10 μg and 30 μg dose amount groups and was comprised mainly of IFNγ+IL-2+ TNFα+, IFNγ+IL-2+ TNFα−, and IFNγ+IL-2-TNFα− cells whereas at the 50 μg dose amount the cytokine profile was mainly composed of IFNγ+IL-2+ TNFα+, IFNγ+IL-2-TNFα+, and IFNγ+IL-2-TNFα− cells (FIG. 13E).

Figure 13C:
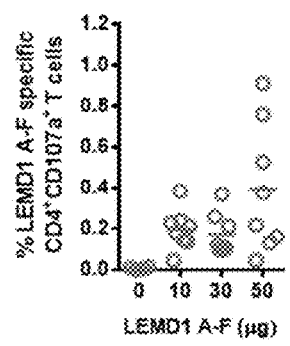
Figure 13D:
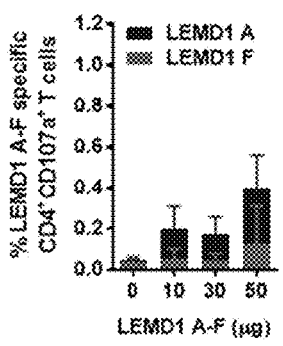
FIG. 13D compares the relative frequency of CD4+CD107a+ T-cells induced by synthetic consensus LEMD1A and synthetic consensus LEMD1F.
Figure 13E:
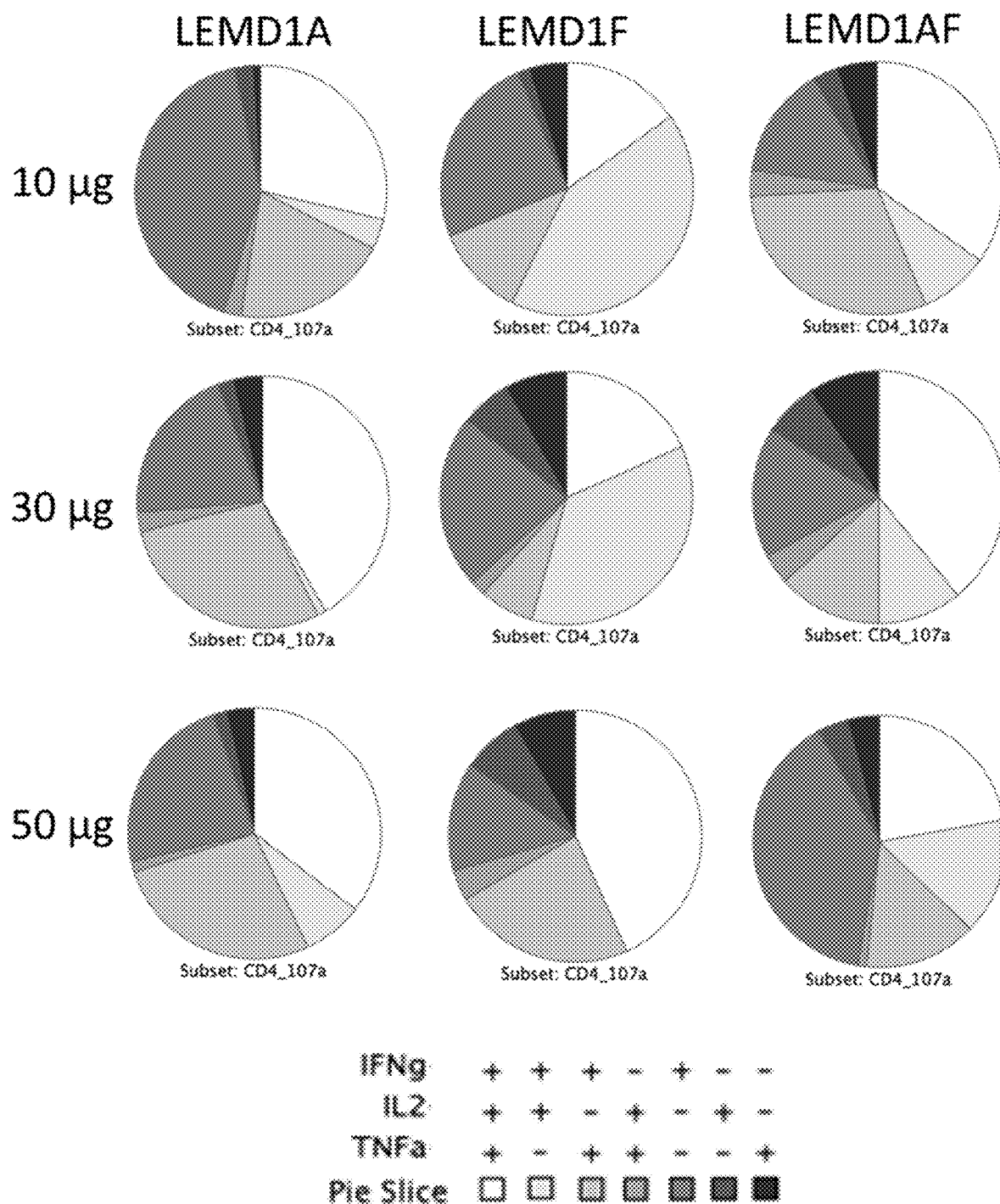
FIG. 13E illustrates the cytokine profile induced in CD4+CD107a+ by pGX1431, pGX1432, and pGX1433.

The frequency of pGX1433 antigen specific CD4+ CD107a+ T cells was 0.20%±0.10%, 0.17%±0.10%, and 0.39%±0.31% in the 10 μg (p=0.365), 30 μg (p=0.992), and 50 μg (p=0.109) dose amount groups, respectively (FIG. 13C). The cytokine profile of pGX1433 specific CD4+ CD107a+ T cells was similar at the 10 μg and 30 μg dose amount groups and was comprised mostly of IFNγ+IL-2+ TNFα+, with some IFNγ+IL-2-TNFα+ and IFNγ+IL-2-TNFα− cells whereas the 50 μg dose amount group was comprised mainly of IFNγ+IL-2-TNFα− with IFNγ+IL-2+ TNFα+, IFNγ+IL-2+ TNFα−, and IFNγ+IL-2-TNFα+ (FIG. 13E).

The frequency of antigen specific CD4+CD107+ T cells is further detailed in Table 9.

TABLE 9

| Construct | Dose | % CD4+ ± Std. Dev. | p-value | % CD4+CD107a+ ± Std. Dev. | p-value |
|---|---|---|---|---|---|
| Synthetic Consensus LEMD1A (pGX1431) | | | | | |
| pGX0001 | 30 μg | 0.04 ± 0.03 | n/a | 0.00 ± 0.00 | n/a |
| pGX1431 | 10 μg | 0.50 ± 0.17 | 0.346 | 0.17 ± 0.09 | 0.532 |
|  | 30 μg | 1.02 ± 0.57 | 0.122 | 0.34 ± 0.19 | 0.314 |
|  | 50 μg | 1.34 ± 0.58 | 0.005 | 0.50 ± 0.30 | 0.002 |
| Synthetic Consensus LEMD1F (pGX1432) | | | | | |
| pGX0001 | 30 μg | 0.06 ± 0.02 | n/a | 0.01 ± 0.00 | n/a |
| pGX1432 | 10 μg | 0.27 ± 0.34 | n/a | 0.10 ± 0.14 | n/a |
|  | 30 μg | 0.24 ± 0.10 | n/a | 0.11 ± 0.08 | n/a |
|  | 50 μg | 0.20 ± 0.20 | n/a | 0.04 ± 0.03 | n/a |

TABLE 9-continued

| Construct | Dose | % CD4+ ± Std. Dev. | p-value | % CD4+CD107a+ ± Std. Dev. | p-value |
|---|---|---|---|---|---|
| Synthetic Consensus LEMD1AF (pGX1433) | | | | | |
| pGX0001 | 30 µg | 0.09 ± 0.03 | n/a | 0.01 ± 0.01 | n/a |
| pGX1433 | 10 µg | 0.53 ± 0.19 | 0.135 | 0.20 ± 0.10 | 0.365 |
|  | 30 µg | 0.50 ± 0.20 | 0.176 | 0.17 ± 0.10 | 0.992 |
|  | 50 µg | 0.80 ± 0.51 | 0.006 | 0.39 ± 0.31 | 0.109 | p-values reported are relative to naïve (pGX0001 immunized mice). Significance in assumed at p ≤ 0.05.

Figure 14A:
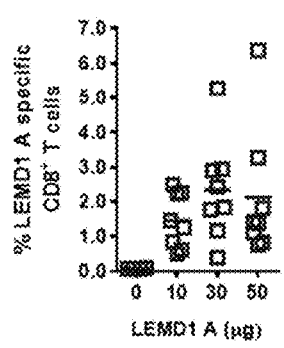
FIG. 14A, FIG. 14B, and FIG. 14C graphically illustrate the relative frequencies of CD8+ T-cells induced by LEMD1A (synthetic consensus pGX1431), LEMD1F (synthetic consensus pGX1432), and LEMD1AF (synthetic consensus pGX1433).
Figure 14B:
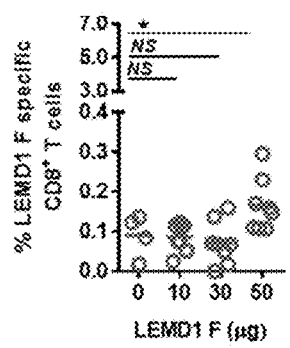

Synthetic consensus LEMD1A induced frequencies of antigen specific CD8+ T cell responses that were more robust than naïve (0.08%±0.01%) but not significant at the 10 µg (1.46%±0.79%), 30 µg (2.34%±1.47%), and 50 µg (2.12%±1.897%) dose amount groups (FIG. 14A). Synthetic consensus LEMD1A specific CD8+ T cell responses were dose-independent and consisted mainly of IFNγ+IL-2-TNFα- and some IFNγ+IL-2-TNFα+ producing CD8+ T cells (FIG. 14E).

Synthetic consensus LEMD1F induced frequencies of antigen specific CD8+ T cell responses that were not greater than naïve (0.09%±0.05%). Specifically, pGX1432 induced non-significant responses at the 10 µg dose amount (0.09%±0.04%), 30 µg (0.07%±0.05%) and 50 µg (0.17%±0.07%) dose amount groups (FIG. 14B). Synthetic consensus LEMD1F specific CD8+ T cell responses were dose-independent and consisted mainly of IFNγ-IL-2+-TNFα-, IFNγ-IL-2-TNFα+, and IFNγ+IL-2-TNFα- producing CD8+ T cells (FIG. 14E).

Figure 14C:
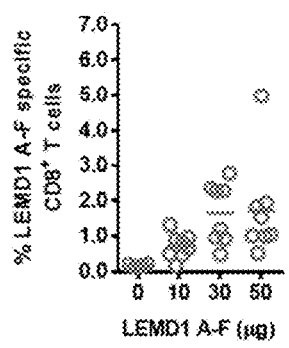
Figure 14D:
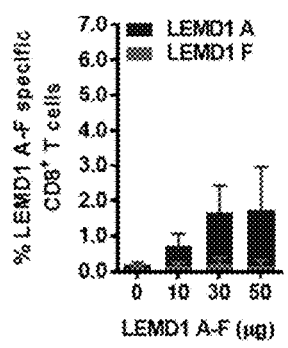
FIG. 14D compares the relative frequency of CD8+ T-cells induced by synthetic consensus LEMD1A and synthetic consensus LEMD1F.
Figure 14E:
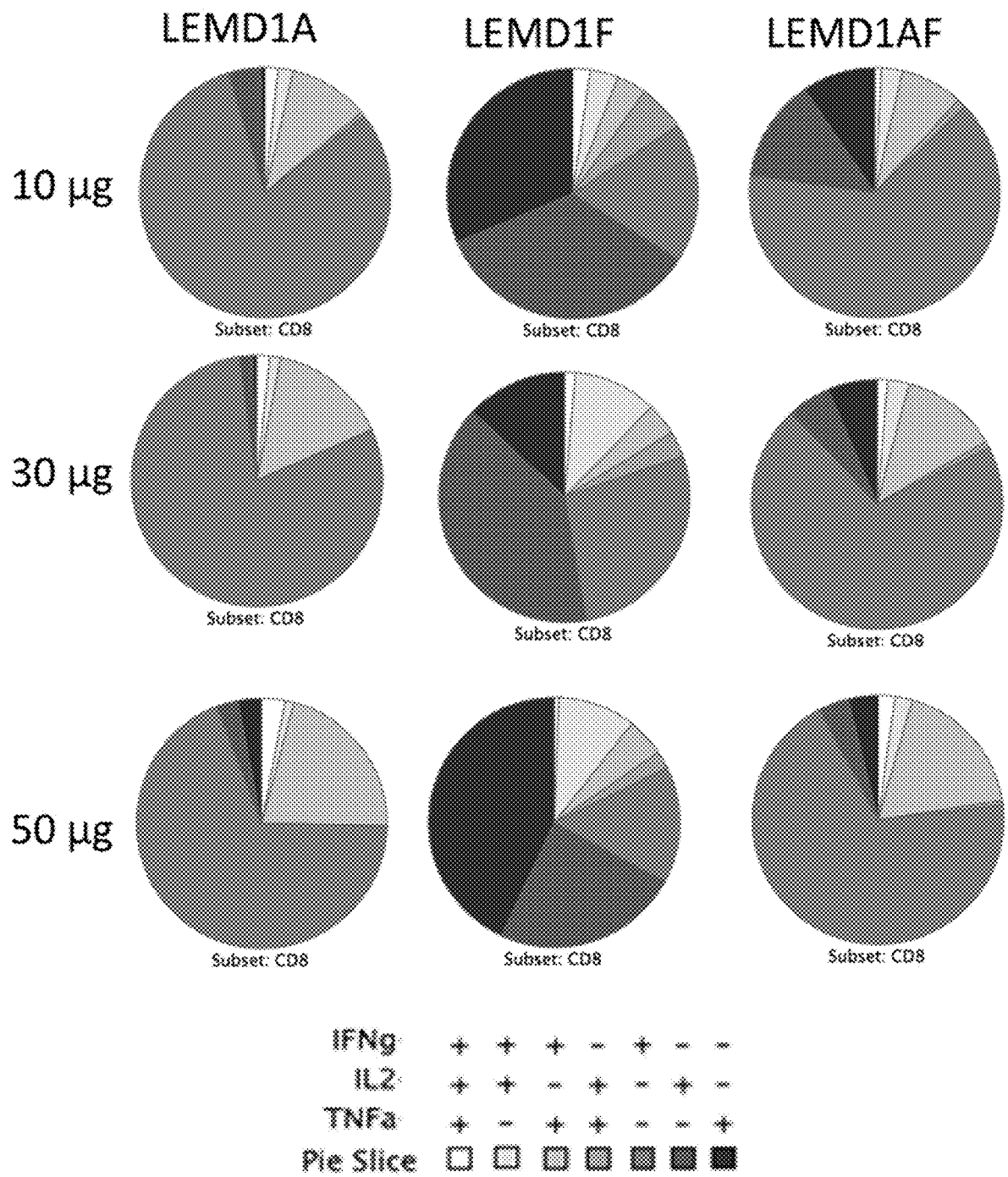
FIG. 14E illustrates the cytokine profile induced by synthetic consensus LEMD1A, LEMD1F, and LEMD1AF in the CD8+ T-cell compartment.

Synthetic consensus LEMD1AF induced frequencies of antigen specific CD8+ T cell responses that were significantly more robust than naïve (0.17%±0.043%) at the 50 µg dose amount (1.73%±1.40%) (p=0.046) but not at the 10 µg (0.72%±0.36%) (p=0.061) or 30 µg (1.65%±0.86%) (p=0.061) dose amount groups (FIG. 14C). Synthetic consensus LEMD1AF specific CD8+ T cell responses were dose-dependent and consisted mainly of IFNγ+IL-2-TNFα- and some IFNγ+IL-2-TNFα+ and IFNγ-IL-2+-TNFα-producing CD8+ T cells (FIG. 14E).

The frequency of antigen specific CD8+ T cells is further detailed in Table 10.

TABLE 10

| Construct | Dose | % CD8+ ± Std. Dev. | p-value | % CD8+CD107a+ ± Std. Dev. | p-value |
|---|---|---|---|---|---|
| Synthetic Consensus LEMD1A (pGX1431) | | | | | |
| pGX0001 | 30 µg | 0.08 ± 0.01 | n/a | 0.03 ± 0.03 | n/a |
| pGX1431 | 10 µg | 1.46 ± 0.79 | n/a | 1.37 ± 0.78 | n/a |
|  | 30 µg | 2.34 ± 1.47 | n/a | 2.23 ± 1.45 | n/a |
|  | 50 µg | 2.12 ± 1.89 | n/a | 1.97 ± 1.84 | n/a |
| Synthetic Consensus LEMD1F (pGX1432) | | | | | |
| pGX0001 | 30 µg | 0.09 ± 0.05 | n/a | 0.04 ± 0.02 | n/a |
| pGX1432 | 10 µg | 0.09 ± 0.04 | n/a | 0.02 ± 0.02 | n/a |
|  | 30 µg | 0.07 ± 0.05 | n/a | 0.05 ± 0.04 | n/a |
|  | 50 µg | 0.17 ± 0.07 | n/a | 0.04 ± 0.03 | n/a |
| Synthetic Consensus LEMD1AF (pGX1433) | | | | | |
| pGX0001 | 30 µg | 0.17 ± 0.04 | n/a | 0.07 ± 0.01 | n/a |
| pGX1433 | 10 µg | 0.72 ± 0.36 | 0.760 | 0.54 ± 0.39 | 0.897 |
|  | 30 µg | 1.65 ± 0.86 | 0.061 | 1.43 ± 1.39 | 0.089 |
|  | 50 µg | 1.73 ± 1.40 | 0.046 | 1.57 ± 1.39 | 0.053 | p-values reported are relative to naïve (pGX0001 immunized mice). Significance in assumed at p ≤ 0.05.

The synthetic consensus LEMD1 constructs pGX1431 and pGX1433, but not pGX1432, induced a frequency of CD8+CD107a+ T cells that was greater than naïve but were not significant at any dose amount.

Figure 15A:
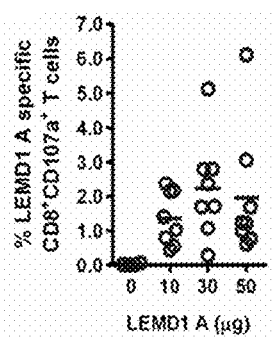
FIG. 15A, FIG. 15B, and FIG. 15C graphically illustrate the cytolytic potential of antigen specific CD8+CD107a+ T-cells induced by synthetic consensus LEMD1A, synthetic consensus LEMD1F, and synthetic consensus LEMD1AF, respectively.

Specifically, the frequency of pGX1431 antigen specific CD8+CD107a+ T cells was 1.37%±0.78%, 2.23%±1.45%, and 1.97%±1.84% in the 10 µg, 30 µg, and 50 µg dose amounts groups, respectively (FIG. 15A). The cytokine profile of pGX1431 specific CD8+CD107a+ T cells was similar across dose amount groups and was comprised mainly of IFNγ+IL-2-TNFα- and some IFNγ+IL-2-TNFα+ cells (FIG. 15E).

Figure 15B:
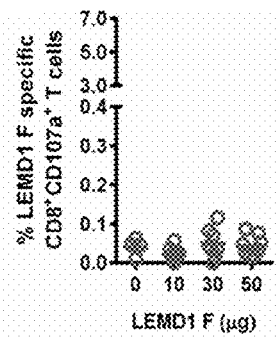

The frequency of pGX1432 antigen specific CD8+CD107a+ T cells was 0.02%±0.02%, 0.05%±0.04%, and 0.04%±0.03% in the 10 µg, 30 µg, and 50 µg dose amount groups, respectively (FIG. 15B). The cytokine profile of pGX1432 specific CD8+CD107a+ T cells was comprised mainly of IFNγ+IL-2-TNFα-, IFNγ-IL-2+ TNFα-, and IFNγ+IL-2+ TNFα- cells (FIG. 15E).

Figure 15C:
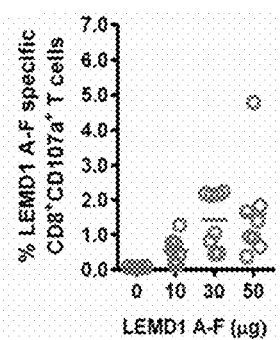
Figure 15D:
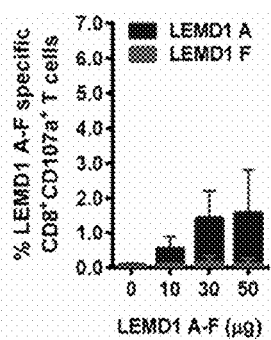
FIG. 15D compares the relative frequency of CD8+CD107a+ T-cells induced by synthetic consensus LEMD1A and synthetic consensus LEMD1F.
Figure 15E:
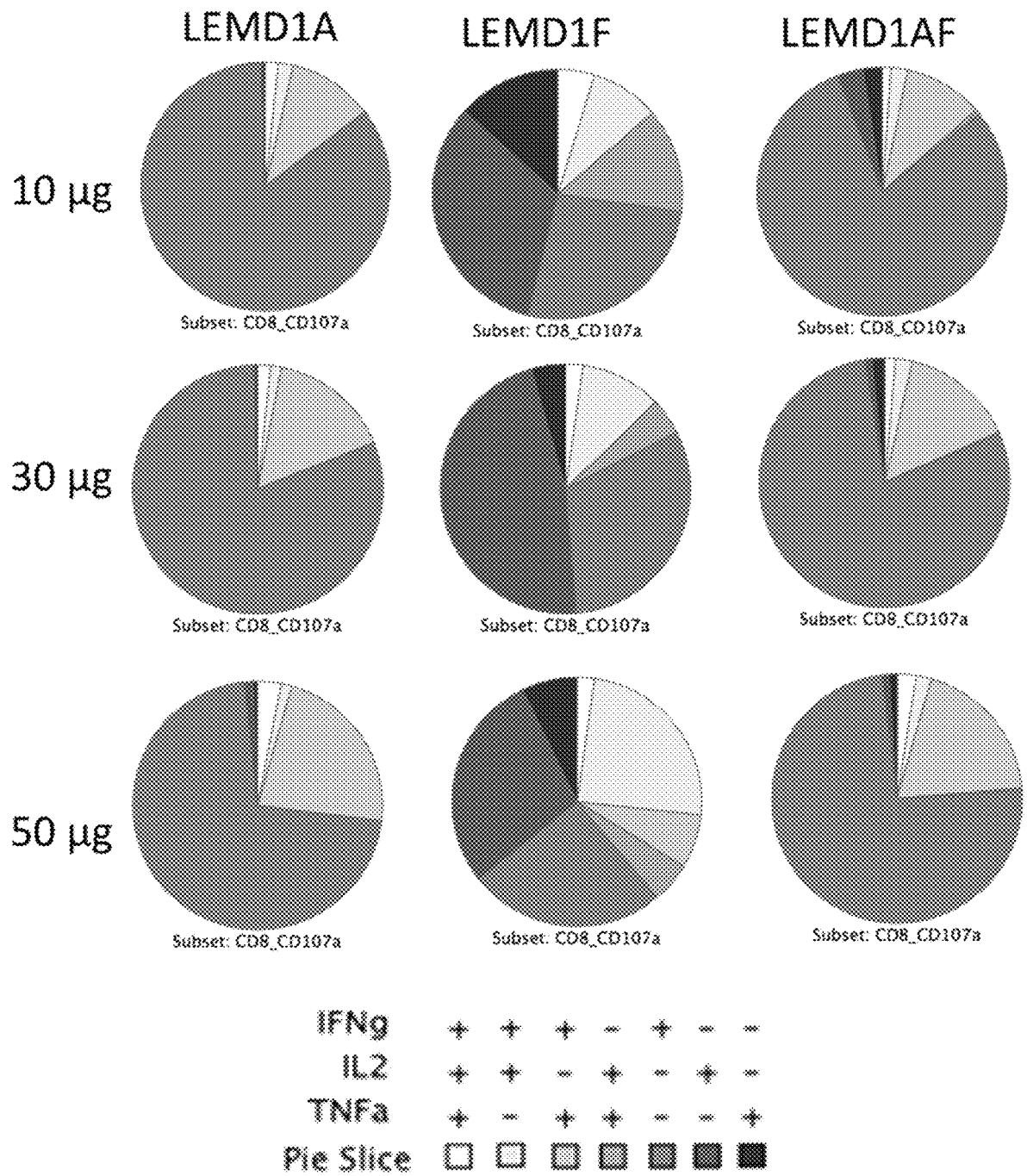
FIG. 15E illustrates the cytokine profile induced in CD8+CD107a+ by LEMD1A (synthetic consensus pGX1431), LEMD1F (synthetic consensus pGX1432), and LEMD1AF (synthetic consensus pGX1433).

The frequency of pGX1433 antigen specific CD8+CD107a+ T cells was 0.54%±0.39%, 1.43%±1.39%, and 1.57%±1.39% in the 10 µg (p=0.897), 30 µg (p=0.089), and 50 µg (p=0.053) dose amount groups, respectively (FIG. 15C). The cytokine profile of pGX1433 specific CD8+CD107a+ T cells was comprised mostly of IFNγ+IL-2-TNFα- and some IFNγ+IL-2-TNFα+ cells (FIG. 15E).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modification to the disclosed embodiments, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule comprising one or more nucleic acid sequences selected from the group consisting of:
   (a) a nucleic acid sequence that encodes amino acid residues 19 to 198 of SEQ ID NO: 2;
   (b) a nucleic acid sequence that encodes amino acid residues 19 to 84 of SEQ ID NO: 4;
   (c) a nucleic acid sequence that encodes amino acid residues 19 to 198 and 206 to 271 of SEQ ID NO: 6;
   (d) a nucleic acid sequence that encodes a fragment comprising at least 90% of an entire length of a protein that is 100% identical to amino acid residues 19 to 198 of SEQ ID NO: 2 and comprises at least one alanine amino acid residue at a position corresponding to position 37, 42, or 51 of SEQ ID NO: 2;
   (e) a nucleic acid sequence that encodes a fragment comprising at least 90% of an entire length of a protein that is 100% identical to amino acid residues 19 to 84 of SEQ ID NO: 4 and comprises at least one alanine amino acid residue at a position corresponding to position 37 or 42 of SEQ ID NO: 4;
   (f) a nucleic acid sequence that encodes a fragment comprising at least 90% of an entire length of a protein that is 100% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(g) a nucleic acid sequence that encodes a protein that is greater than 96% identical to amino acid residues 19 to 198 of SEQ ID NO: 2 and comprises at least one alanine amino acid residue at a position corresponding to position 37, 42, or 51 of SEQ ID NO: 2;

(h) a nucleic acid sequence that encodes a protein that is greater than 96% identical to amino acid residues 19 to 84 of SEQ ID NO: 4 and comprises at least one alanine amino acid residue at a position corresponding to position 37 or 42 of SEQ ID NO: 4;

(i) a nucleic acid sequence that encodes a protein that is at least 95% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(j) a nucleic acid sequence that encodes a fragment comprising at least 90% of an entire length of a protein that is greater than 95.6% identical to amino acid residues 19 to 198 of SEQ ID NO: 2 and comprises at least one alanine amino acid residue at a position corresponding to position 37, 42, or 51 of SEQ ID NO: 2;

(k) a nucleic acid sequence that encodes a fragment comprising at least 90% of an entire length of a protein that is greater than 95.5% identical to amino acid residues 19 to 84 of SEQ ID NO: 4 and comprises at least one alanine amino acid residue at a position corresponding to position 37 or 42 of SEQ ID NO: 4; and (l) a nucleic acid sequence that encodes a fragment comprising at least 90% of an entire length of a protein that is at least 95% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6.

2. A vector comprising a nucleic acid molecule comprising one or more nucleic acid sequences selected from the group consisting of:

(a) a nucleic acid sequence that encodes amino acid residues 19 to 198 of SEQ ID NO: 2;

(b) a nucleic acid sequence that encodes amino acid residues 19 to 84 of SEQ ID NO: 4;

(c) a nucleic acid sequence that encodes amino acid residues 19 to 198 and 206 to 271 of SEQ ID NO: 6;

(d) a nucleic acid sequence that encodes a fragment comprising at least 90% of an entire length of a protein that is 100% identical to amino acid residues 19 to 198 of SEQ ID NO: 2 and comprises at least one alanine amino acid residue at a position corresponding to position 37, 42, or 51 of SEQ ID NO: 2;

(e) a nucleic acid sequence that encodes a fragment comprising at least 90% of an entire length of a protein that is 100% identical to amino acid residues 19 to 84 of SEQ ID NO: 4 and comprises at least one alanine amino acid residue at a position corresponding to position 37 or 42 of SEQ ID NO: 4;

(f) a nucleic acid sequence that encodes a fragment comprising at least 90% of an entire length of a protein that is 100% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(g) a nucleic acid sequence that encodes a protein that is greater than 96% identical to amino acid residues 19 to 198 of SEQ ID NO: 2 and comprises at least one alanine amino acid residue at a position corresponding to position 37, 42, or 51 of SEQ ID NO: 2;

(h) a nucleic acid sequence that encodes a protein that is greater than 96% identical to amino acid residues 19 to 84 of SEQ ID NO: 4 and comprises at least one alanine amino acid residue at a position corresponding to position 37 or 42 of SEQ ID NO: 4;

(i) a nucleic acid sequence that encodes a protein that is at least 95% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(j) a nucleic acid sequence that encodes a fragment comprising at least 90% of an entire length of a protein that is greater than 95.6% identical to amino acid residues 19 to 198 of SEQ ID NO: 2 and comprises at least one alanine amino acid residue at a position corresponding to position 37, 42, or 51 of SEQ ID NO: 2;

(k) a nucleic acid sequence that encodes a fragment comprising at least 90% of an entire length of a protein that is greater than 95.5% identical to amino acid residues 19 to 84 of SEQ ID NO: 4 and comprises at least one alanine amino acid residue at a position corresponding to position 37 or 42 of SEQ ID NO: 4;

(l) a nucleic acid sequence that encodes a fragment comprising at least 90% of an entire length of a protein that is at least 95% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(m) nucleotides 55 to 600 of SEQ ID NO: 1;

(n) nucleotides 55 to 258 of SEQ ID NO: 3;

(o) nucleotides 55 to 594 and 616 to 819 of SEQ ID NO: 5;

(p) a fragment comprising at least 90% of an entire length of a nucleic acid molecule that is 100% identical to nucleotides 55 to 600 of SEQ ID NO: 1, wherein the fragment encodes an alanine at amino acid position 37, 42, or 51 relative to SEQ ID NO: 2;

(q) a fragment comprising at least 90% of an entire length of a nucleic acid molecule that is 100% identical to nucleotides 55 to 258 of SEQ ID NO: 3, wherein the fragment encodes an alanine at amino acid position 37 or 42 relative to SEQ ID NO: 4;

(r) a fragment comprising at least 90% of an entire length of a nucleic acid molecule that is 100% identical to nucleotides 55 to 594 and 616 to 819 of SEQ ID NO: 5 wherein the fragment encodes an alanine at amino acid position 37, 42, 51, 224, or 229 relative to SEQ ID NO: 6;

(s) a fragment that is at least 95% identical to nucleotides 55 to 600 of SEQ ID NO: 1, wherein the fragment encodes an alanine at amino acid position 37, 42, or 51 relative to SEQ ID NO: 2;

(t) a fragment that is at least 95% identical to nucleotides 55 to 258 of SEQ ID NO: 3, wherein the fragment encodes an alanine at amino acid position 37 or 42 relative to SEQ ID NO: 4;

(u) a fragment that is at least 95% identical to nucleotides 55 to 594 and 616 to 819 of SEQ ID NO: 5, wherein the fragment encodes an alanine at amino acid position 37, 42, 51, 224, or 229 relative to SEQ ID NO: 6;

(v) a fragment comprising at least 90% of an entire length of a nucleic acid sequence that is at least 95% identical to nucleotides 55 to 600 of SEQ ID NO: 1, wherein the fragment encodes an alanine at amino acid position 37, 42, or 51 relative to SEQ ID NO: 2;

(w) a fragment comprising at least 90% of an entire length of a nucleic acid sequence that is at least 95% identical to nucleotides 55 to 258 of SEQ ID NO: 3, wherein the fragment encodes an alanine at amino acid position 37 or 42 relative to SEQ ID NO: 4; and (x) a fragment comprising at least 90% of an entire length of a nucleic acid sequence that is at least 95% identical to nucleotides 55 to 594 and 616 to 819 of SEQ ID NO: 5, wherein the fragment encodes an alanine at amino acid position 37, 42, 51, 224, or 229 relative to SEQ ID NO: 6.

3. The vector of claim 2 wherein the vector is a plasmid or a viral vector.

4. The vector of claim 2, wherein the nucleic acid molecule is operably linked to a regulatory element selected from a promoter and a poly-adenylation signal.

5. The vector of claim 4, wherein the promoter is a human cytomegalovirus immediate-early promoter (hCMV promoter).

6. The vector of claim 4, wherein the poly-adenylation signal is a bovine growth hormone poly-adenylation signal (bGH polyA).

7. A composition comprising one or more nucleic acid molecules comprising one or more nucleic acid sequences selected from the group consisting of:

(a) a nucleic acid sequence that encodes amino acid residues 19 to 198 of SEQ ID NO: 2;

(b) a nucleic acid sequence that encodes amino acid residues 19 to 84 of SEQ ID NO: 4;

(c) a nucleic acid sequence that encodes amino acid residues 19 to 198 and 206 to 271 of SEQ ID NO: 6;

(d) a nucleic acid sequence that encodes a fragment comprising at least 90% of an entire length of a protein that is 100% identical to amino acid residues 19 to 198 of SEQ ID NO: 2 and comprises at least one alanine amino acid residue at a position corresponding to position 37, 42, or 51 of SEQ ID NO: 2;

(e) a nucleic acid sequence that encodes a fragment comprising at least 90% of an entire length of a protein that is 100% identical to amino acid residues 19 to 84 of SEQ ID NO: 4 and comprises at least one alanine amino acid residue at a position corresponding to position 37 or 42 of SEQ ID NO: 4;

(f) a nucleic acid sequence that encodes a fragment comprising at least 90% of an entire length of a protein that is 100% identical to comprising amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(g) a nucleic acid sequence that encodes a protein that is greater than 96% identical to amino acid residues 19 to 198 of SEQ ID NO: 2 and comprises at least one alanine amino acid residue at a position corresponding to position 37, 42, or 51 of SEQ ID NO: 2;

(h) a nucleic acid sequence that encodes a protein that is greater than 96% identical to amino acid residues 19 to 84 of SEQ ID NO: 4 and comprises at least one alanine amino acid residue at a position corresponding to position 37 or 42 of SEQ ID NO: 4;

(i) a nucleic acid sequence that encodes a protein that is at least 95% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(j) a nucleic acid sequence that encodes a fragment comprising at least 90% of an entire length of a protein that is greater than 95.6% identical to amino acid residues 19 to 198 of SEQ ID NO: 2 and comprises at least one alanine amino acid residue at a position corresponding to position 37, 42, or 51 of SEQ ID NO: 2;

(k) a nucleic acid sequence that encodes a fragment comprising at least 90% of an entire length of a protein that is greater than 95.5% identical to amino acid residues 19 to 84 of SEQ ID NO: 4 and comprises at least one alanine amino acid residue at a position corresponding to position 37 or 42 of SEQ ID NO: 4;

(l) a nucleic acid sequence that encodes a fragment comprising at least 90% of an entire length of a protein that is at least 95% identical to amino acid residues 19 to 198 and 206 to 271 of SEQ ID NO: 6 and comprises at least one alanine amino acid residue at a position corresponding to position 37, 42, 51, 224, or 229 of SEQ ID NO: 6;

(m) nucleotides 55 to 600 of SEQ ID NO: 1;

(n) nucleotides 55 to 258 of SEQ ID NO: 3;

(o) nucleotides 55 to 594 and 616 to 819 of SEQ ID NO: 5;

(p) a fragment comprising at least 90% of an entire length of a nucleic acid molecule that is 100% identical to nucleotides 55 to 600 of SEQ ID NO: 1, wherein the fragment encodes an alanine at amino acid position 37, 42, or 51 relative to SEQ ID NO: 2;

(q) a fragment comprising at least 90% of an entire length of a nucleic acid molecule that is 100% identical to nucleotides 55 to 258 of SEQ ID NO: 3, wherein the fragment encodes an alanine at amino acid position 37 or 42 relative to SEQ ID NO: 4;

(r) a fragment comprising at least 90% of an entire length of a nucleic acid molecule that is 100% identical to nucleotides 55 to 594 and 616 to 819 of SEQ ID NO: 5, wherein the fragment encodes an alanine at amino acid position 37, 42, 51, 224, or 229 relative to SEQ ID NO: 6;

(s) a fragment that is at least 95% identical to nucleotides 55 to 600 of SEQ ID NO: 1, wherein the fragment encodes an alanine at amino acid position 37, 42, or 51 relative to SEQ ID NO: 2;

(t) a fragment that is at least 95% identical to nucleotides 55 to 258 of SEQ ID NO: 3, wherein the fragment encodes an alanine at amino acid position 37 or 42 relative to SEQ ID NO: 4;

(u) a fragment that is at least 95% identical to nucleotides 55 to 594 and 616 to 819 of SEQ ID NO: 5, wherein the fragment encodes an alanine at amino acid position 37, 42, 51, 224, or 229 relative to SEQ ID NO: 6;

(v) a fragment comprising at least 90% of an entire length of a nucleic acid sequence that is at least 95% identical to nucleotides 55 to 600 of SEQ ID NO: 1, wherein the fragment encodes an alanine at amino acid position 37, 42, or 51 relative to SEQ ID NO: 2;

(w) a fragment comprising at least 90% of an entire length of a nucleic acid sequence that is at least 95% identical to nucleotides 55 to 258 of SEQ ID NO: 3, wherein the fragment encodes an alanine at amino acid position 37 or 42 relative to SEQ ID NO: 4; and (x) a fragment comprising at least 90% of an entire length of a nucleic acid sequence that is at least 95% identical to nucleotides 55 to 594 and 616 to 819 of SEQ ID NO: 5, wherein the fragment encodes an alanine at amino acid position 37, 42, 51, 224, or 229 relative to SEQ ID NO: 6.

8. A composition comprising the vector of claim 2.

9. The composition of claim 7 further comprising a pharmaceutically acceptable carrier.

10. The composition of claim 8 further comprising a pharmaceutically acceptable carrier.

11. A vaccine comprising the vector of claim 2.

12. The vaccine of claim 11, wherein the vector comprises an expression vector.

13. The vaccine of claim 11, comprising a pharmaceutically acceptable excipient.

14. The vaccine of claim 11, comprising an adjuvant.

15. The vaccine of claim 14, wherein the adjuvant is IL-12, IL-15, IL-28, or RANTES.

16. A vaccine comprising the nucleic acid molecule of claim 1.

17. The vaccine of claim 16, wherein the nucleic acid molecule comprises an expression vector.

18. The vaccine of claim 16, comprising a pharmaceutically acceptable excipient.

19. The vaccine of claim 16, comprising an adjuvant.

20. The vaccine of claim 19, wherein the adjuvant is IL-12, IL-15, IL-28, or RANTES.

* * * * *

SEQUENCE LISTING

<160> NUMBER OF SEQ ID NOS: 16

<210> SEQ ID NO 1
<211> LENGTH: 600
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic consensus LEMD1A DNA Sequence"

<400> SEQUENCE: 1

| | | | | | |
|---|---|---|---|---|---|
| atggactgga | cctggattct | gttcctggtg | gcagcagcaa | cacgggtgca | ctccgtggac | 60 |
| gtgaagtgcc | tgtctgattg | taagctgcag | aaccagctgg | agaagctggc | ctttagccct | 120 |
| ggcgccatcc | tgccatccac | caggaagctg | gccgagaaga | agctggtgca | gctgctggtg | 180 |
| tccccacctt | gcgcaccacc | cgtgatgaat | ggaccccgcg | agctggacgg | agcacaggat | 240 |
| agcgacgatt | ccgaggagct | gaacatcatc | ctgcagggca | atatcatcct | gtctaccgag | 300 |
| aagagcaaga | agctgaagaa | gcggcccgag | gcctctacca | caaagcctaa | ggccgtggac | 360 |
| acatactgcc | tggattataa | gccatctaag | ggccggagat | gggcagccag | ggccccaagc | 420 |
| acccgcatca | catacggcac | catcacaaag | gagcgggact | attgtaccga | ggatcagaca | 480 |
| gccgagagct | ggagagagga | gggcttccct | gtgggcctga | agctggccgt | gctgggcatc | 540 |
| ttcatcatcg | tggtgttcgt | gtacctgaca | gtggagaaca | agccactgtt | tggctgataa | 600 |

<210> SEQ ID NO 2
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic consensus LEMD1A Protein Sequence"

<400> SEQUENCE: 2

Met Asp Trp Thr Trp Ile Leu Phe Leu Val Ala Ala Thr Arg Val
1               5                   10                  15

His Ser Val Asp Val Lys Cys Leu Ser Asp Cys Lys Leu Gln Asn Gln
            20                  25                  30

Leu Glu Lys Leu Ala Phe Ser Pro Gly Ala Ile Leu Pro Ser Thr Arg
        35                  40                  45

Lys Leu Ala Glu Lys Lys Leu Val Gln Leu Leu Val Ser Pro Pro Cys
    50                  55                  60

Ala Pro Pro Val Met Asn Gly Pro Arg Glu Leu Asp Gly Ala Gln Asp
65                  70                  75                  80

Ser Asp Asp Ser Glu Glu Leu Asn Ile Ile Leu Gln Gly Asn Ile Ile
                85                  90                  95

Leu Ser Thr Glu Lys Ser Lys Lys Leu Lys Lys Arg Pro Glu Ala Ser
            100                 105                 110

Thr Thr Lys Pro Lys Ala Val Asp Thr Tyr Cys Leu Asp Tyr Lys Pro
        115                 120                 125

Ser Lys Gly Arg Arg Trp Ala Ala Arg Ala Pro Ser Thr Arg Ile Thr
    130                 135                 140

Tyr Gly Thr Ile Thr Lys Glu Arg Asp Tyr Cys Thr Glu Asp Gln Thr
145                 150                 155                 160

Ala Glu Ser Trp Arg Glu Glu Gly Phe Pro Val Gly Leu Lys Leu Ala
                165                 170                 175

Val Leu Gly Ile Phe Ile Ile Val Val Phe Val Tyr Leu Thr Val Glu
            180                 185                 190

Asn Lys Pro Leu Phe Gly
        195

<210> SEQ ID NO 3
<211> LENGTH: 258
<212> TYPE: DNA

<213> ORGANISM: Artificial Sequence
<220> FEATURE:
<221> NAME/KEY: source
<223> OTHER INFORMATION: /note="Description of Artificial Sequence: Synthetic consensus LEMD1F DNA Sequence"

<400> SEQUENCE: 3

```
atggactgga cctggattct gttcctggtg gcagcagcaa caagggtgca ctctgtggac      60
gtgaagtgcc tgagcgattg taagctgcag aaccagctgg agaagctggc cttttcccca     120
ggagcaatcc tgagggact gcaggagcac caggcaccag agagccacat gggactgtcc      180
cctaagcggg agaccacagc aaggaagacc agactgctga gggcaggaga agaaggtg       240
tctcagtggg cctgataa                                                   258
```

<210> SEQ ID NO 4
<211> LENGTH: 84
<212> TYPE: PRT
<213> ORGANISM: Artificial Sequence
<220> FEATURE:
<221> NAME/KEY: source
<223> OTHER INFORMATION: /note="Description of Artificial Sequence: Synthetic consensus LEMD1F Protein Sequence"

<400> SEQUENCE: 4

```
Met Asp Trp Thr Trp Ile Leu Phe Leu Val Ala Ala Ala Thr Arg Val
1               5                   10                  15
His Ser Val Asp Val Lys Cys Leu Ser Asp Cys Lys Leu Gln Asn Gln
            20                  25                  30
Leu Glu Lys Leu Ala Phe Ser Pro Gly Ala Ile Leu Arg Gly Leu Gln
        35                  40                  45
Glu His Gln Ala Pro Glu Ser His Met Gly Leu Ser Pro Lys Arg Glu
    50                  55                  60
Thr Thr Ala Arg Lys Thr Arg Leu Leu Arg Ala Gly Glu Lys Lys Val
65                  70                  75                  80
Ser Gln Trp Ala
```

<210> SEQ ID NO 5
<211> LENGTH: 819
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus LEMD1AF DNA Sequence"

<400> SEQUENCE: 5

```
atggactgga cctggattct gttcctggtg gcagcagcaa cccgcgtgca ttccgtcgat      60
gtgaagtgtc tgagtgattg taaactgcag aaccagctgg agaagctggc ctttagccct     120
ggagcaatcc tgccatccac caggaagctg gccgagaaga agctggtgca gctgctggtg     180
agcccacctt gcgcaccacc cgtgatgaat ggcccaagag agctggacgg cgcccaggat     240
agcgacgatt ccgaggagct gaacatcatc ctgcagggca atatcatcct gtctaccgag     300
aagagcaaga agctgaagaa gcggcccgag gcctccacca aaagcctaa ggccgtggac      360
acatactgcc tggattataa gccttccaag ggccggagat gggcagccag ggcccccatct     420
accaggatca catacggcac catcacaaag gagcgggact attgtaccga ggatcagaca     480
gccgagtctt ggagagagga gggattccca gtgggcctga gctgccgt gctgggcatc       540
ttcatcatcg tggtgttcgt gtacctgaca gtggagaaca agcctctgtt tggccggggc     600
```

-continued

```
agaaagaggc gctctgtgga tgtaaaatgc ctatcggact gcaagttgca aaatcaatta    660
gaaaaattgg ccttctcccc agggcgata ttgaggggcc tgcaggagca ccaggcacca    720
gagtcccaca tgggcctgtc tcccaagcgc gagacaaccg caagaaaaac aaggctgctg    780
agggctgggg aaagaaagt gtcacagtgg gcatgataa                           819
```

```
<210> SEQ ID NO 6
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus LEMD1AF Protein Sequence"

<400> SEQUENCE: 6
```

```
Met Asp Trp Thr Trp Ile Leu Phe Leu Val Ala Ala Thr Arg Val
1               5                  10                  15

His Ser Val Asp Val Lys Cys Leu Ser Asp Cys Lys Leu Gln Asn Gln
            20                  25                  30

Leu Glu Lys Leu Ala Phe Ser Pro Gly Ala Ile Leu Pro Ser Thr Arg
        35                  40                  45

Lys Leu Ala Glu Lys Lys Leu Val Gln Leu Leu Val Ser Pro Pro Cys
    50                  55                  60

Ala Pro Pro Val Met Asn Gly Pro Arg Glu Leu Asp Gly Ala Gln Asp
65                  70                  75                  80

Ser Asp Asp Ser Glu Glu Leu Asn Ile Ile Leu Gln Gly Asn Ile Ile
                85                  90                  95

Leu Ser Thr Glu Lys Ser Lys Lys Leu Lys Lys Arg Pro Glu Ala Ser
            100                 105                 110

Thr Thr Lys Pro Lys Ala Val Asp Thr Tyr Cys Leu Asp Tyr Lys Pro
        115                 120                 125

Ser Lys Gly Arg Arg Trp Ala Ala Arg Ala Pro Ser Thr Arg Ile Thr
    130                 135                 140

Tyr Gly Thr Ile Thr Lys Glu Arg Asp Tyr Cys Thr Glu Asp Gln Thr
145                 150                 155                 160

Ala Glu Ser Trp Arg Glu Glu Gly Phe Pro Val Gly Leu Lys Leu Ala
                165                 170                 175

Val Leu Gly Ile Phe Ile Ile Val Val Phe Val Tyr Leu Thr Val Glu
            180                 185                 190

Asn Lys Pro Leu Phe Gly Arg Gly Arg Lys Arg Arg Ser Val Asp Val
        195                 200                 205

Lys Cys Leu Ser Asp Cys Lys Leu Gln Asn Gln Leu Glu Lys Leu Ala
    210                 215                 220

Phe Ser Pro Gly Ala Ile Leu Arg Gly Leu Gln Glu His Gln Ala Pro
225                 230                 235                 240

Glu Ser His Met Gly Leu Ser Pro Lys Arg Glu Thr Thr Ala Arg Lys
                245                 250                 255

Thr Arg Leu Leu Arg Ala Gly Glu Lys Lys Val Ser Gln Trp Ala
            260                 265                 270
```

```
<210> SEQ ID NO 7
<211> LENGTH: 3554
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic pGX1431 sequence"

<400> SEQUENCE: 7

| | | | | | | |
|---|---|---|---|---|---|---|
| gctgcttcgc | gatgtacggg | ccagatatac | gcgttgacat | tgattattga | ctagttatta | 60 |
| atagtaatca | attacggggt | cattagttca | tagcccatat | atggagttcc | gcgttacata | 120 |
| acttacggta | aatggcccgc | ctggctgacc | gcccaacgac | ccccgcccat | tgacgtcaat | 180 |
| aatgacgtat | gttcccatag | taacgccaat | agggactttc | cattgacgtc | aatgggtgga | 240 |
| gtatttacgg | taaactgccc | acttggcagt | acatcaagtg | tatcatatgc | caagtacgcc | 300 |
| ccctattgac | gtcaatgacg | gtaaatggcc | cgcctggcat | tatgcccagt | acatgacctt | 360 |
| atgggacttt | cctacttggc | agtacatcta | cgtattagtc | atcgctatta | ccatggtgat | 420 |
| gcggttttgg | cagtacatca | atgggcgtgg | atagcggttt | gactcacggg | gatttccaag | 480 |
| tctccacccc | attgacgtca | atgggagttt | gttttggcac | caaaatcaac | gggactttcc | 540 |
| aaaatgtcgt | aacaactccg | ccccattgac | gcaaatgggc | ggtaggcgtg | tacggtggga | 600 |
| ggtctatata | agcagagctc | tctggctaac | tagagaaccc | actgcttact | ggcttatcga | 660 |
| aattaatacg | actcactata | gggagaccca | agctggctag | cgtttaaact | taagcttggt | 720 |
| accgagctcg | gatccgccac | catggactgg | acctggattc | tgttcctggt | ggcagcagca | 780 |
| acacgggtgc | actccgtgga | cgtgaagtgc | ctgtctgatt | gtaagctgca | gaaccagctg | 840 |
| gagaagctgg | cctttagccc | tggcgccatc | ctgccatcca | ccaggaagct | ggccgagaag | 900 |
| aagctggtgc | agctgctggt | gtccccacct | tgcgcaccac | ccgtgatgaa | tggaccccgc | 960 |
| gagctggacg | gagcacagga | tagcgacgat | tccgaggagc | tgaacatcat | cctgcagggc | 1020 |
| aatatcatcc | tgtctaccga | gaagagcaag | aagctgaaga | agcggcccga | ggcctctacc | 1080 |
| acaaagccta | aggccgtgga | cacatactgc | ctggattata | agccatctaa | gggccggaga | 1140 |
| tgggcagcca | gggccccaag | cacccgcatc | acatacggca | ccatcacaaa | ggagcgggac | 1200 |
| tattgtaccg | aggatcagac | agccgagagc | tggagagagg | agggcttccc | tgtgggcctg | 1260 |
| aagctggccg | tgctgggcat | cttcatcatc | gtggtgttcg | tgtacctgac | agtggagaac | 1320 |
| aagccactgt | ttggctgata | actcgagtct | agagggcccg | tttaaacccg | ctgatcagcc | 1380 |
| tcgactgtgc | cttctagttg | ccagccatct | gttgtttgcc | cctcccccgt | gccttccttg | 1440 |
| accctggaag | gtgccactcc | cactgtcctt | tcctaataaa | atgaggaaat | tgcatcgcat | 1500 |
| tgtctgagta | ggtgtcattc | tattctgggg | ggtggggtgg | ggcaggacag | caaggggag | 1560 |
| gattgggaag | acaatagcag | gcatgctggg | gatgcggtgg | gctctatggc | ttctactggg | 1620 |
| cggttttatg | gacagcaagc | gaaccggaat | tgccagctgg | ggcgccctct | ggtaaggttg | 1680 |
| ggaagcccctg | caaagtaaac | tggatggctt | tcttgccgcc | aaggatctga | tggcgcaggg | 1740 |
| gatcaagctc | tgatcaagag | acaggatgag | gatcgtttcg | catgattgaa | caagatggat | 1800 |
| tgcacgcagg | ttctccggcc | gcttgggtgg | agaggctatt | cggctatgac | tgggcacaac | 1860 |
| agacaatcgg | ctgctctgat | gccgccgtgt | tccggctgtc | agcgcagggg | cgcccggttc | 1920 |
| tttttgtcaa | gaccgacctg | tccggtgccc | tgaatgaact | gcaagacgag | gcagcgcggc | 1980 |
| tatcgtggct | ggccacgacg | ggcgttcctt | gcgcagctgt | gctcgacgtt | gtcactgaag | 2040 |
| cgggaaggga | ctggctgcta | ttgggcgaag | tgccggggca | ggatctcctg | tcatctcacc | 2100 |
| ttgctcctgc | cgagaaagta | tccatcatgg | ctgatgcaat | gcggcggctg | catacgcttg | 2160 |
| atccggctac | ctgcccattc | gaccaccaag | cgaaacatcg | catcgagcga | gcacgtactc | 2220 |
| ggatggaagc | cggtcttgtc | gatcaggatg | atctggacga | agagcatcag | gggctcgcgc | 2280 |

```
cagccgaact gttcgccagg ctcaaggcga gcatgcccga cggcgaggat ctcgtcgtga    2340
cccatggcga tgcctgcttg ccgaatatca tggtggaaaa tggccgcttt tctggattca    2400
tcgactgtgg ccggctgggt gtggcggacc gctatcagga catagcgttg gctacccgtg    2460
atattgctga agagcttggc ggcgaatggg ctgaccgctt cctcgtgctt tacggtatcg    2520
ccgctcccga ttcgcagcgc atcgccttct atcgccttct tgacgagttc ttctgaatta    2580
ttaacgctta caatttcctg atgcggtatt ttctccttac gcatctgtgc ggtatttcac    2640
accgcatcag gtggcacttt cggggaaat gtgcgcggaa ccctattg tttatttttc       2700 taaatacatt caaatatgta tccgctcatg agacaataac cctgataaat gcttcaataa    2760
tagcacgtgc taaaacttca tttttaattt aaaaggatct aggtgaagat ccttttgat     2820 aatctcatga ccaaaatccc ttaacgtgag ttttcgttcc actgagcgtc agacccgta     2880 gaaaagatca aggatcttc ttgagatcct ttttttctgc gcgtaatctg ctgcttgcaa     2940
acaaaaaaac caccgctacc agcggtggtt tgtttgccgg atcaagagct accaactctt    3000
tttccgaagg taactggctt cagcagagcg cagataccaa atactgttct tctagtgtag    3060
ccgtagttag gccaccactt caagaactct gtagcaccgc ctacatacct cgctctgcta    3120
atcctgttac cagtggctgc tgccagtggc gataagtcgt gtcttaccgg gttggactca    3180
agacgatagt taccggataa ggcgcagcgg tcgggctgaa cggggggttc gtgcacacag    3240
cccagcttgg agcgaacgac ctacaccgaa ctgagatacc tacagcgtga gctatgagaa    3300
agcgccacgc ttcccgaagg gagaaaggcg gacaggtatc cggtaagcgg cagggtcgga    3360
acaggagagc gcacgaggga gcttccaggg ggaaacgcct ggtatcttta tagtcctgtc    3420
gggtttcgcc acctctgact tgagcgtcga ttttgtgat gctcgtcagg ggggcggagc    3480
ctatggaaaa acgccagcaa cgcggccttt ttacggttcc tggccttttg ctggccttt     3540 gctcacatgt tctt                                                      3554
```

<210> SEQ ID NO 8  
<211> LENGTH: 3212  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic pGX1432 sequence"

<400> SEQUENCE: 8

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
```

-continued

| | | | | | |
|---|---|---|---|---|---|
| aattaatacg | actcactata | gggagaccca | agctggctag | cgtttaaact | taagcttggt | 720 |
| accgagctcg | gatccgccac | catggactgg | acctggattc | tgttcctggt | ggcagcagca | 780 |
| acaagggtgc | actctgtgga | cgtgaagtgc | ctgagcgatt | gtaagctgca | gaaccagctg | 840 |
| gagaagctgg | ccttttcccc | aggagcaatc | ctgaggggac | tgcaggagca | ccaggcacca | 900 |
| gagagccaca | tgggactgtc | ccctaagcgg | gagaccacag | caaggaagac | cagactgctg | 960 |
| agggcaggag | agaagaaggt | gtctcagtgg | gcctgataac | tcgagtctag | agggcccgtt | 1020 |
| taaacccgct | gatcagcctc | gactgtgcct | tctagttgcc | agccatctgt | tgtttgcccc | 1080 |
| tcccccgtgc | cttccttgac | cctggaaggt | gccactccca | ctgtcctttc | ctaataaaat | 1140 |
| gaggaaattg | catcgcattg | tctgagtagg | tgtcattcta | ttctgggggg | tggggtgggg | 1200 |
| caggacagca | aggggagga | ttgggaagac | aatagcaggc | atgctgggga | tgcggtgggc | 1260 |
| tctatggctt | ctactgggcg | gttttatgga | cagcaagcga | accggaattg | ccagctgggg | 1320 |
| cgccctctgg | taaggttggg | aagccctgca | aagtaaactg | gatggctttc | ttgccgccaa | 1380 |
| ggatctgatg | gcgcagggga | tcaagctctg | atcaagagac | aggatgagga | tcgtttcgca | 1440 |
| tgattgaaca | agatggattg | cacgcaggtt | ctccggccgc | ttgggtggag | aggctattcg | 1500 |
| gctatgactg | ggcacaacag | acaatcggct | gctctgatgc | cgccgtgttc | cggctgtcag | 1560 |
| cgcaggggcg | cccggttctt | tttgtcaaga | ccgacctgtc | cggtgccctg | aatgaactgc | 1620 |
| aagacgaggc | agcgcggcta | tcgtggctgg | ccacgacggg | cgttccttgc | gcagctgtgc | 1680 |
| tcgacgttgt | cactgaagcg | ggaagggact | ggctgctatt | gggcgaagtg | ccggggcagg | 1740 |
| atctcctgtc | atctcaccett | gctcctgccg | agaaagtatc | catcatggct | gatgcaatgc | 1800 |
| ggcggctgca | tacgcttgat | ccggctacct | gcccattcga | ccaccaagcg | aaacatcgca | 1860 |
| tcgagcgagc | acgtactcgg | atggaagccg | gtcttgtcga | tcaggatgat | ctggacgaag | 1920 |
| agcatcaggg | gctcgcgcca | gccgaactgt | tcgccaggct | caaggcgagc | atgcccgacg | 1980 |
| gcgaggatct | cgtcgtgacc | catggcgatg | cctgcttgcc | gaatatcatg | gtggaaaatg | 2040 |
| gccgcttttc | tggattcatc | gactgtggcc | ggctgggtgt | ggcggaccgc | tatcaggaca | 2100 |
| tagcgttggc | tacccgtgat | attgctgaag | agcttggcgg | cgaatgggct | gaccgcttcc | 2160 |
| tcgtgcttta | cggtatcgcc | gctcccgatt | cgcagcgcat | cgccttctat | cgccttcttg | 2220 |
| acgagttctt | ctgaattatt | aacgcttaca | atttcctgat | gcggtatttt | ctccttacgc | 2280 |
| atctgtgcgg | tatttcacac | cgcatcaggt | ggcacttttc | ggggaaatgt | gcgcggaacc | 2340 |
| cctatttgtt | tatttttcta | aatacattca | aatatgtatc | cgctcatgag | acaataaccc | 2400 |
| tgataaatgc | ttcaataata | gcacgtgcta | aaacttcatt | tttaatttaa | aaggatctag | 2460 |
| gtgaagatcc | ttttttgataa | tctcatgacc | aaaatccctt | aacgtgagtt | ttcgttccac | 2520 |
| tgagcgtcag | accccgtaga | aaagatcaaa | ggatcttctt | gagatccttt | ttttctgcgc | 2580 |
| gtaatctgct | gcttgcaaac | aaaaaaacca | ccgctaccag | cggtggtttg | tttgccggat | 2640 |
| caagagctac | caactctttt | tccgaaggta | actggcttca | gcagagcgca | gataccaaat | 2700 |
| actgttcttc | tagtgtagcc | gtagttaggc | caccacttca | agaactctgt | agcaccgcct | 2760 |
| acatacctcg | ctctgctaat | cctgttacca | gtggctgctg | ccagtggcga | taagtcgtgt | 2820 |
| cttaccgggt | tggactcaag | acgatagtta | ccggataagg | cgcagcggtc | gggctgaacg | 2880 |
| gggggttcgt | gcacacagcc | cagcttggag | cgaacgacct | acaccgaact | gagatacccta | 2940 |
| cagcgtgagc | tatgagaaag | cgccacgctt | cccgaaggga | gaaaggcgga | caggtatccg | 3000 |
| gtaagcggca | gggtcggaac | aggagagcgc | acgagggagc | ttccaggggg | aaacgcctgg | 3060 |

<210> SEQ ID NO 9
<211> LENGTH: 3773
<212> TYPE: DNA
<213> ORGANISM: Artificial Sequence
<220> FEATURE:
<221> NAME/KEY: source
<223> OTHER INFORMATION: /note="Description of Artificial Sequence: Synthetic pGX1433 sequence"

<400> SEQUENCE: 9

```
tatctttata gtcctgtcgg gtttcgccac ctctgacttg agcgtcgatt tttgtgatgc    3120
tcgtcagggg ggcggagcct atggaaaaac gccagcaacg cggccttttt acggttcctg    3180
gccttttgct ggccttttgc tcacatgttc tt                                  3212 gctgcttcgc gatgtacggg ccagatatac gcgttgacat tgattattga ctagttatta      60
atagtaatca attacggggt cattagttca tagcccatat atggagttcc gcgttacata     120
acttacggta atggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggactgg acctggattc tgttcctggt ggcagcagca     780
acccgcgtgc attccgtcga tgtgaagtgt ctgagtgatt gtaaactgca gaaccagctg     840
gagaagctgg cctttagccc tggagcaatc ctgccatcca ccaggaagct ggccgagaag     900
aagctggtgc agctgctggt gagcccacct tgcgcaccac ccgtgatgaa tggcccaaga     960
gagctggacg cgcccagga tagcgacgat tccgaggagc tgaacatcat cctgcagggc    1020
aatatcatcc tgtctaccga aaagagcaag aagctgaaga gcggcccga ggcctccacc    1080
acaaagccta aggccgtgga cacatactgc ctggattata gccttccaa gggccggaga    1140
tgggcagcca gggccccatc taccaggatc acatacggca ccatcacaaa ggagcgggac    1200
tattgtaccg aggatcagac agccgagtct tggagagagg agggattccc agtgggcctg    1260
aagctggccg tgctgggcat cttcatcatc gtggtgttcg tgtacctgac agtggagaac    1320
aagcctctgt ttggccgggg cagaaagagg cgctctgtgg atgtaaaatg cctatcggac    1380
tgcaagttgc aaaatcaatt agaaaaattg gccttctccc caggggcgat attgagggc     1440
ctgcaggagc accaggcacc agagtcccac atgggcctgt ctcccaagcg cgagacaacc    1500
gcaagaaaaa caaggctgct gagggctggg gaaaagaaag tgtcacagtg gcatgataa     1560
ctcgagtcta gagggcccgt ttaaacccgc tgatcagcct cgactgtgcc ttctagttgc    1620
cagccatctg ttgtttgccc ctcccccgtg ccttccttga ccctggaagg tgccactccc    1680
actgtccttt cctaataaaa tgaggaaatt gcatcgcatt gtctgagtag gtgtcattct    1740
attctggggg gtggggtggg gcaggacagc aaggggggagg attgggaaga caatagcagg    1800
```

| | |
|---|---|
| catgctgggg atgcggtggg ctctatggct tctactgggc ggttttatgg acagcaagcg | 1860 |
| aaccggaatt gccagctggg gcgccctctg gtaaggttgg gaagccctgc aaagtaaact | 1920 |
| ggatggcttt cttgccgcca aggatctgat ggcgcagggg atcaagctct gatcaagaga | 1980 |
| caggatgagg atcgtttcgc atgattgaac aagatggatt gcacgcaggt tctccggccg | 2040 |
| cttgggtgga gaggctattc ggctatgact gggcacaaca gacaatcggc tgctctgatg | 2100 |
| ccgccgtgtt ccggctgtca gcgcaggggc gcccggttct ttttgtcaag accgacctgt | 2160 |
| ccggtgccct gaatgaactg caagacgagg cagcgcggct atcgtggctg gccacgacgg | 2220 |
| gcgttccttg cgcagctgtg ctcgacgttg tcactgaagc gggaagggac tggctgctat | 2280 |
| tgggcgaagt gccggggcag gatctcctgt catctcacct tgctcctgcc gagaaagtat | 2340 |
| ccatcatggc tgatgcaatg cggcggctgc atacgcttga tccggctacc tgcccattcg | 2400 |
| accaccaagc gaaacatcgc atcgagcgag cacgtactcg gatggaagcc ggtcttgtcg | 2460 |
| atcaggatga tctggacgaa gagcatcagg ggctcgcgcc agccgaactg ttcgccaggc | 2520 |
| tcaaggcgag catgcccgac ggcgaggatc tcgtcgtgac ccatggcgat gcctgcttgc | 2580 |
| cgaatatcat ggtggaaaat ggccgctttt ctggattcat cgactgtggc cggctgggtg | 2640 |
| tggcggaccg ctatcaggac atagcgttgg ctacccgtga tattgctgaa gagcttggcg | 2700 |
| gcgaatgggc tgaccgcttc ctcgtgcttt acggtatcgc cgctcccgat tcgcagcgca | 2760 |
| tcgccttcta tcgccttctt gacgagttct tctgaattat taacgcttac aatttcctga | 2820 |
| tgcggtattt tctccttacg catctgtgcg gtatttcaca ccgcatcagg tggcactttt | 2880 |
| cggggaaatg tgcgcggaac ccctatttgt ttatttttct aaatacattc aaatatgtat | 2940 |
| ccgctcatga gacaataacc ctgataaatg cttcaataat agcacgtgct aaaacttcat | 3000 |
| ttttaattta aaaggatcta ggtgaagatc ctttttgata tctcatgac caaaatccct | 3060 |
| taacgtgagt tttcgttcca ctgagcgtca gaccccgtag aaaagatcaa aggatcttct | 3120 |
| tgagatcctt ttttttctgcg cgtaatctgc tgcttgcaaa caaaaaaacc accgctacca | 3180 |
| gcggtggttt gtttgccgga tcaagagcta ccaactcttt ttccgaaggt aactggcttc | 3240 |
| agcagagcgc agataccaaa tactgttctt ctagtgtagc cgtagttagg ccaccacttc | 3300 |
| aagaactctg tagcaccgcc tacatacctc gctctgctaa tcctgttacc agtggctgct | 3360 |
| gccagtggcg ataagtcgtg tcttaccggg ttggactcaa gacgatagtt accggataag | 3420 |
| gcgcagcggt cgggctgaac ggggggttcg tgcacacagc ccagcttgga gcgaacgacc | 3480 |
| tacaccgaac tgagatacct acagcgtgag ctatgagaaa gcgccacgct tcccgaaggg | 3540 |
| agaaaggcgg acaggtatcc ggtaagcggc agggtcggaa caggagagcg cacgagggag | 3600 |
| cttccagggg gaaacgcctg gtatctttat agtcctgtcg ggtttcgcca cctctgactt | 3660 |
| gagcgtcgat ttttgtgatg ctcgtcaggg gggcggagcc tatggaaaaa cgccagcaac | 3720 |
| gcggcctttt tacggttcct ggccttttgc tggccttttg ctcacatgtt ctt | 3773 |

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic Furin cleavage site sequence"

<400> SEQUENCE: 10

Arg Gly Arg Lys Arg Arg Ser

<210> SEQ ID NO 11
<211> LENGTH: 198
<212> TYPE: PRT
<213> ORGANISM: Homo sapiens
<220> FEATURE:
<221> NAME/KEY: source
<223> OTHER INFORMATION: /note="Native Human LEMD1A Protein Sequence"

<400> SEQUENCE: 11

Met Asp Trp Thr Trp Ile Leu Phe Leu Val Ala Ala Ala Thr Arg Val
1               5                   10                  15

His Ser Val Asp Val Lys Cys Leu Ser Asp Cys Lys Leu Gln Asn Gln
            20                  25                  30

Leu Glu Lys Leu Gly Phe Ser Pro Gly Pro Ile Leu Pro Ser Thr Arg
        35                  40                  45

Lys Leu Tyr Glu Lys Lys Leu Val Gln Leu Leu Val Ser Pro Pro Cys
    50                  55                  60

Ala Pro Pro Val Met Asn Gly Pro Arg Glu Leu Asp Gly Ala Gln Asp
65                  70                  75                  80

Ser Asp Asp Ser Glu Glu Leu Asn Ile Ile Leu Gln Gly Asn Ile Ile
                85                  90                  95

Leu Ser Thr Glu Lys Ser Lys Lys Leu Lys Lys Trp Pro Glu Ala Ser
            100                 105                 110

Thr Thr Lys Arg Lys Ala Val Asp Thr Tyr Cys Leu Asp Tyr Lys Pro
        115                 120                 125

Ser Lys Gly Arg Arg Trp Ala Ala Arg Ala Pro Ser Thr Arg Ile Thr
    130                 135                 140

Tyr Gly Thr Ile Thr Lys Glu Arg Asp Tyr Cys Ala Glu Asp Gln Thr
145                 150                 155                 160

Ile Glu Ser Trp Arg Glu Gly Phe Pro Val Gly Leu Lys Leu Ala
                165                 170                 175

Val Leu Gly Ile Phe Ile Ile Val Phe Val Tyr Leu Thr Val Glu
            180                 185                 190

Asn Lys Ser Leu Phe Gly
            195

<210> SEQ ID NO 12
<211> LENGTH: 84
<212> TYPE: PRT
<213> ORGANISM: Homo sapiens
<220> FEATURE:
<221> NAME/KEY: source
<223> OTHER INFORMATION: /note="Native Human LEMD1F Protein Sequence"

<400> SEQUENCE: 12

Met Asp Trp Thr Trp Ile Leu Phe Leu Val Ala Ala Ala Thr Arg Val
1               5                   10                  15

His Ser Val Asp Val Lys Cys Leu Ser Asp Cys Lys Leu Gln Asn Gln
            20                  25                  30

Leu Glu Lys Leu Gly Phe Ser Pro Gly Pro Ile Leu Arg Gly Leu Gln
        35                  40                  45

Glu His Gln Ala Pro Glu Ser His Met Gly Leu Ser Pro Lys Arg Glu
    50                  55                  60

Thr Thr Ala Arg Lys Thr Arg Leu Ser Arg Ala Gly Glu Lys Lys Val
65                  70                  75                  80

Ser Gln Trp Ala

<210> SEQ ID NO 13
<211> LENGTH: 181
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

Met Val Asp Val Lys Cys Leu Ser Asp Cys Lys Leu Gln Asn Gln Leu
1               5                   10                  15

Glu Lys Leu Ala Phe Ser Pro Gly Ala Ile Leu Pro Ser Thr Arg Lys
            20                  25                  30

Leu Ala Glu Lys Lys Leu Val Gln Leu Leu Val Ser Pro Pro Cys Ala
        35                  40                  45

Pro Pro Val Met Asn Gly Pro Arg Glu Leu Asp Gly Ala Gln Asp Ser
    50                  55                  60

Asp Asp Ser Glu Glu Leu Asn Ile Ile Leu Gln Gly Asn Ile Ile Leu
65                  70                  75                  80

Ser Thr Glu Lys Ser Lys Lys Leu Lys Lys Arg Pro Glu Ala Ser Thr
                85                  90                  95

Thr Lys Pro Lys Ala Val Asp Thr Tyr Cys Leu Asp Tyr Lys Pro Ser
            100                 105                 110

Lys Gly Arg Arg Trp Ala Ala Arg Ala Pro Ser Thr Arg Ile Thr Tyr
        115                 120                 125

Gly Thr Ile Thr Lys Glu Arg Asp Tyr Cys Thr Glu Asp Gln Thr Ala
    130                 135                 140

Glu Ser Trp Arg Glu Glu Gly Phe Pro Val Gly Leu Lys Leu Ala Val
145                 150                 155                 160

Leu Gly Ile Phe Ile Ile Val Val Phe Val Tyr Leu Thr Val Glu Asn
                165                 170                 175

Lys Pro Leu Phe Gly
            180

<210> SEQ ID NO 14
<211> LENGTH: 181
<212> TYPE: PRT
<213> ORGANISM: Homo sapiens

<400> SEQUENCE: 14

Met Val Asp Val Lys Cys Leu Ser Asp Cys Lys Leu Gln Asn Gln Leu
1               5                   10                  15

Glu Lys Leu Gly Phe Ser Pro Gly Pro Ile Leu Pro Ser Thr Arg Lys
            20                  25                  30

Leu Tyr Glu Lys Lys Leu Val Gln Leu Leu Val Ser Pro Pro Cys Ala
        35                  40                  45

Pro Pro Val Met Asn Gly Pro Arg Glu Leu Asp Gly Ala Gln Asp Ser
    50                  55                  60

Asp Asp Ser Glu Glu Leu Asn Ile Ile Leu Gln Gly Asn Ile Ile Leu
65                  70                  75                  80

Ser Thr Glu Lys Ser Lys Lys Leu Lys Lys Trp Pro Glu Ala Ser Thr
                85                  90                  95

Thr Lys Arg Lys Ala Val Asp Thr Tyr Cys Leu Asp Tyr Lys Pro Ser
            100                 105                 110

Lys Gly Arg Arg Trp Ala Ala Arg Ala Pro Ser Thr Arg Ile Thr Tyr

```
                  115                 120                 125
Gly Thr Ile Thr Lys Glu Arg Asp Tyr Cys Ala Glu Asp Gln Thr Ile
        130                 135                 140

Glu Ser Trp Arg Glu Glu Gly Phe Pro Val Gly Leu Lys Leu Ala Val
145                 150                 155                 160

Leu Gly Ile Phe Ile Ile Val Val Phe Val Tyr Leu Thr Val Glu Asn
                165                 170                 175

Lys Ser Leu Phe Gly
            180

<210> SEQ ID NO 15
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Val Asp Val Lys Cys Leu Ser Asp Cys Lys Leu Gln Asn Gln Leu
1               5                   10                  15

Glu Lys Leu Ala Phe Ser Pro Gly Ala Ile Leu Arg Gly Leu Gln Glu
            20                  25                  30

His Gln Ala Pro Glu Ser His Met Gly Leu Ser Pro Lys Arg Glu Thr
        35                  40                  45

Thr Ala Arg Lys Thr Arg Leu Leu Arg Ala Gly Glu Lys Lys Val Ser
    50                  55                  60

Gln Trp Ala
65

<210> SEQ ID NO 16
<211> LENGTH: 67
<212> TYPE: PRT
<213> ORGANISM: Homo sapiens

<400> SEQUENCE: 16

Met Val Asp Val Lys Cys Leu Ser Asp Cys Lys Leu Gln Asn Gln Leu
1               5                   10                  15

Glu Lys Leu Gly Phe Ser Pro Gly Pro Ile Leu Arg Gly Leu Gln Glu
            20                  25                  30

His Gln Ala Pro Glu Ser His Met Gly Leu Ser Pro Lys Arg Glu Thr
        35                  40                  45

Thr Ala Arg Lys Thr Arg Leu Ser Arg Ala Gly Glu Lys Lys Val Ser
    50                  55                  60

Gln Trp Ala
65
```